(12) United States Patent
Takimiya et al.

(10) Patent No.: US 7,834,198 B2
(45) Date of Patent: Nov. 16, 2010

(54) CONDENSED POLYCYCLIC AROMATIC COMPOUND AND USE THEREOF

(75) Inventors: Kazuo Takimiya, Higashihiroshima (JP); Yoshihito Kunugi, Higashihiroshima (JP); Yasushi Konda, Higashihiroshima (JP)

(73) Assignee: National University of Corporation Hiroshima University, Higashihiroshioma-shi (JP)

( * ) Notice: Subject to any disclaimer, the term of this patent is extended or adjusted under 35 U.S.C. 154(b) by 687 days.

(21) Appl. No.: 11/814,218

(22) PCT Filed: Jan. 18, 2006

(86) PCT No.: PCT/JP2006/300654

§ 371 (c)(1),
(2), (4) Date: Jul. 18, 2007

(87) PCT Pub. No.: WO2006/077888

PCT Pub. Date: Jul. 27, 2006

(65) Prior Publication Data

US 2009/0001357 A1    Jan. 1, 2009

(30) Foreign Application Priority Data

Jan. 19, 2005    (JP) .............................. 2005-012123

(51) Int. Cl.
*C07D 517/04*    (2006.01)
(52) U.S. Cl. ....................................................... 549/42
(58) Field of Classification Search .................... 549/42
See application file for complete search history.

(56) References Cited

U.S. PATENT DOCUMENTS 3,278,552 A    10/1966    Geering

FOREIGN PATENT DOCUMENTS

| JP | 08 245636 | 9/1996 |
|---|---|---|
| JP | 2001 515933 | 9/2001 |
| JP | 2003 221579 | 8/2003 |
| JP | 2004 002407 | 1/2004 |
| JP | 2004-158709 | 6/2004 |
| JP | 2005-154371 | 6/2005 |
| SU | 755785 | 8/1980 |

OTHER PUBLICATIONS

D. J. Gundlach et al., "Pentacene Organic Thin-Film Transistors-Molecular Ordering and Mobility" IEEE Electron Device Letters, vol. 18, No. 3, Mar. 1997, pp. 87-89.
J. G. Laquindanum et al., "Benzodithiophene Rings as Semiconductor Building Blocks" Advanced Materials, 1997, 9, No. 1, pp. 36-39.
H. Meng et al., "High Field-Effect Mobility Oligofluorene Derivatives with High Environmental Stability" J.Am.Chem. Soc, 2001, 123, pp. 9214-9215.
Ito et al., "Oligo (2, 6-anthrylene)s; Acene-Oligomer Approach for Organic Field-Effect Transistors" Angew.Chem.Int.Ed. 2003.42, No. 10, pp. 1159-1162.
M. Iwaoka et al., "Nature of Nonbonded Se . . . O Interactions Characterized by 17O NMR Spectroscopy and NBO and AIM Analyses" J.Am.Chem.Soc. 2004, 126, pp. 5309-5317.
S. Y. Zherdeva et al., "Synthesis and Transformations of 2, 7-Disubstituted Benzothieno [3.2-b] Benzothiophenes" Plenum Publishing Corporation, 1980, pp. 383-390.
K. Nakasuji et al., "Linear Conjugated Systems Bearing Aromatic Terminal Groups. VIII. Syntheses and Electronic Spectra of Bis(4-biphenylyl)- and 2,2'-Difluorenylpoly-ynes" Bulletin of The Chemical Society of Japan, 1972, vol. 45, pp. 883-891.
M. Hori et al., "10-Thia-anthracenes. Part 3. 1 A Re-examination of the Reaction of 9-Phenyl-thioxanthylium Salt and Phenyl-lithium" J. Chem. Soc. Perkin Trans. I, 1987, pp. 187-193.
H. Sashida et al., "A Simple One-Pot Synthesis of [1]Benzotelluro[3,2-b][1]-benzotellurophenes and its Selenium and Sulfur Analogues from 2,2'-Dibromodiphenylacetylene [1]" J. Heterocyclic Chem, 35, 725, 1998, pp. 725-726.
N. A. Bumagin et al., "Palladium catalyzed cross-coupling reaction of Grignard reagents with halobenzoic acids, halophenols and haloanilines" J. Org. Chem. 532, 1997, pp. 271-273.
J. Kowalik et al., "Diphenylacetylene and the LICKOR Superbase: o,o'-Dimetalation and Reaction with Electrophiles. A Convenient Synthesis of o,o'-Disubstituted Diphenylacetylenes" J. Org. Chem. 2001, 66, pp. 3229-3231.
M. J. Mio et al., "One-Pot Synthesis of Symmetrical and Unsymmetrical Bisarylethynes by a Modification of the Sonogashira Coupling Reaction" Organic Letters, 2002, vol. 4, No. 19, pp. 3199-3202.
P. Kaszynski et al., "Synthesis and Properties of Diethyl 5,10-Dihetera-5,10-dihydroindeno[2,1-a]indene-2,7-dicarboxylates" J. Org. Chem. 1993, 58, pp. 5209-5220.
D. Haristoy, et al., "Structure and photoconductive behaviour of a sanidic liquid crystal", Liquid Crystals, vol. 27, No. 3, XP000932241, Mar. 1, 2000, pp. 321-328.
S. Dobrin, et al., "Photophysics of trans-stilbene analogues: indolo[3,2-b]indole and its heterosubstituted sulfur and selenium derivatives", Chemical Physics, vol. 216, XP002537531, 1997, pp. 179-192.

*Primary Examiner*—Taofiq A Solola
(74) *Attorney, Agent, or Firm*—Oblon, Spivak, McClelland, Maier & Neustadt, L.L.P.

(57) ABSTRACT

The object of the present invention to provide an organic semiconductor device comprising an organic semiconductor material satisfying both the requirement of high electron field-effect mobility and high on/off current ratio. The present invention provides a novel condensed polycyclic aromatic compound satisfying both the high electron field-effect mobility and high on/off current ratio required for organic semiconductor materials.

2 Claims, 4 Drawing Sheets

CONDENSED POLYCYCLIC AROMATIC COMPOUND AND USE THEREOF

CROSS REFERENCE TO RELATED APPLICATION

This application is a 371 of PCT/JP06/300654, filed on Jan. 18, 2006, and claims priority to Japanese Patent Application No. 2005-012123, filed on Jan. 19, 2005.

TECHNICAL FIELD

The present invention relates to organic semiconductor electron materials for use in photoelectric, photoelectronic, electric, and electronic components, for example, relates to organic semiconductor electron materials applicable in devices having an organic semiconductor layer such as thin film transistors (TFT), thin film photoelectric transducers, dye sensitized solar cells, and the like, light emitting devices having an organic carrier transport layer or light emitting layer, and the like devices.

BACKGROUND ART

Recently, many studies have been worked on organic semiconductor devices using organic semiconductor materials as organic electron components (for example, organic electroluminescent (EL) devices, organic FET devices, thin film devices such as organic thin film transistor devices or organic thin film photoelectric converting devices). As a result of studies, some organic semiconductor devices have been put to practical use.

To be improved in their performance, it is important for the organic semiconductors to use an organic semiconductor material having an excellent performance. Accordingly, intensive searches and studies have been carried out for an organic semiconductor material excellent in light emitting property and/or carrier mobility, etc.

In general, a carrier transport ability is required in an organic electron material to be applicable to electric and electronic devices such as organic thin film transistors, etc. For example, the carrier mobility, which influences an efficiency in charge transport, is an important factor for the organic EL device in order to attain highly efficient light emission or low power driving. Furthermore, practical use of the organic FET devices cannot be realized without improvement in the carrier mobility, which directly influences switching speeds and performance of devices to drive.

Organic semiconductors are generally low in the carrier mobility, compared with silicon-based semiconductors. The low carrier mobility gives the organic semiconductors a low response speed. Albeit this has been a hindrance to the practical use of the organic semiconductors, new organic semiconductors have been developed recently, in which a mobility equivalent to that of amorphous silicon is realized.

For example, it was reported that pentacene, which is a polycyclic aromatic molecule consisting of five benzene rings condensed to align straightly, showed high mobility (0.1 to 1.0 $cm^2/Vs$) equivalent to that of amorphous silicon. Because the performance of a pentacene-based TFT is largely dependent on the purity of pentacene, which forms an active layer, the pentacene-based TFT was realized by inevitably conducting sublimation refinement in vacuum or in hydrogen stream in plural times before the production of the device. [See, for example, Non-Patent Citation 1 (IEEE Electron Dev. Lett. 18, 87 (1997))]

Moreover, Non-Patent Citation 2 (Joyce G. Laquindanum et al. Adv. Mater. 9, 36 (1997)) reported that benzodithiophene dimer, that is, the dimer of benzothiophene monomer, showed a mobility of 0.04 $cm^2/Vs$.

Furthermore, it was recently reported that a combination of thiophene and fluorene produced a material having a mobility of 0.14 $cm^2/Vs$. [See, for example, Non-Patent Citation 3 (Z. Boa et al. J. Am. CHEM. Soc. 123, 9214 (2001)). Another recent report demonstrated that mobilities of a dimer or a trimer of anthracene were in the 0.1 $cm^2/Vs$ order. [See, for example, Non-Patent Citation 4 (Suzuki et al. Angew. Chem. Int. Ed. 42, 1159 (2003)). Moreover, electric field effect elements having a semiconductor layer made of a large condensed polycyclic aromatic compound such as ovalene, hexabenzocoronene, circumanthracene or the like, have been reported (Patent Citation 1: Japanese Unexamined Patent Application Publication, Tokukai, No. 2004-158709 (published on Jun. 3, 2004).

DISCLOSURE OF INVENTION

[Technical Problem]

As described above, a strategy to design a molecular structure of an organic semiconductor material having a high mobility has not been established. Instead, existing compounds with or without modification have been mainly utilized as such an organic semiconductor material.

However, the use of pentacene described in Non-Patent Citation 1 has a problem in refining the material. The materials described in Non-Patent Citations 2 to 4 are disadvantageous in that their productions need multi-staged reactions including a low-yield stage. Thus, the materials described in Non-Patent Citations 2 to 4 are not suitable for mass synthesis and need more improvement in their production methods before the materials are used practically. The organic semiconductor materials described in Patent Citation 1 has a drawback in that super high vacuum is necessary to highly refine the material or to form a thin film, because the material has a low vapor pressure. Further, the compound described in Patent Citation 1 has such a structure that a very large number of aromatic rings are condensed. Generally, compounds having such a structure are highly affinitive with oxygen. The high affinity with oxygen makes it difficult to drive a device thereof in the atmosphere.

The present invention was accomplished in view of the aforementioned problems. An object of the present invention is to realize an organic semiconductor material that can be highly purified and/or fabricated into a thin film without requiring a super high vacuum environment. Moreover, the present invention realizes an organic semiconductor material in which a device thereof can be driven in atmosphere.

[Technical Solution]

A compound according to the present invention is a compound represented by:

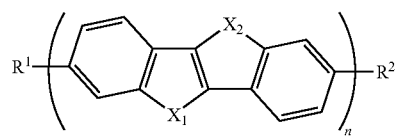

where $X^1$ and $X^2$ are independently a calcogen atom, n is an integer in a range of 1 to 3, and $R^1$ and $R^2$ are independently a halogen, a $C_1$-$C_{18}$ alkyl, a halogenated $C_1$-$C_{18}$ alkyl, a $C_1$-$C_{18}$ alkyloxy, a $C_1$-$C_{18}$ alkylthio, an aryl, or an aryl having at least one selected from the group consisting of a halogen, a $C_1$-$C_{18}$ alkyl, a halogenated $C_1$-$C_{18}$ alkyl, a $C_1$-$C_{18}$ alkyloxy, and a $C_1$-$C_{18}$ alkylthio.

The compound according to the present invention is preferably structured such that the calcogen atom is a sulfur atom, a selenium atom, or tellurium atom.

The compound according to the present invention is preferably structured such that $R^1$ and $R^2$ have independently at least one of a halogen, a $C_1$-$C_{18}$ alkyl, a halogenated $C_1$-$C_{18}$ alkyl, a $C_1$-$C_{18}$ alkyloxy, a $C_1$-$C_{18}$ alkylthio, and an aryl, and are represented by:

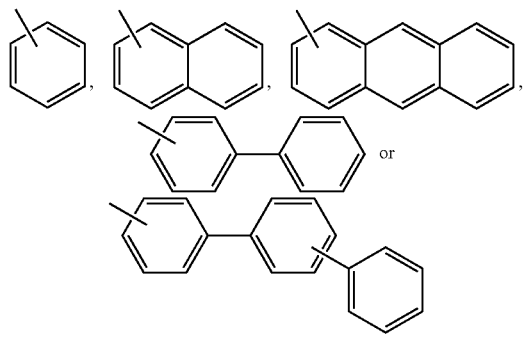

A method according to the present invention is a method of producing a compound, the method using a reaction expressed as Formula:

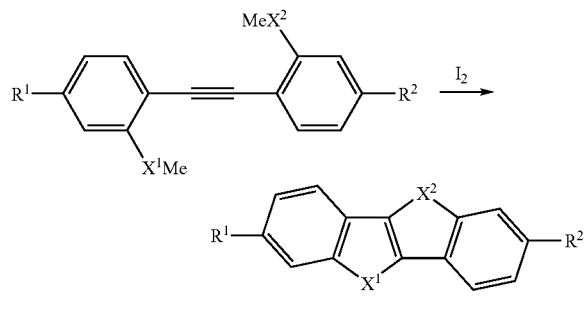

where $X^1$ and $X^2$ are independently a calcogen atom, and $R^1$ and $R^2$ are independently a halogen, a $C_1$-$C_{18}$ alkyl, a halogenated $C_1$-$C_{18}$ alkyl, a $C_1$-$C_{18}$ alkyloxy, a $C_1$-$C_{18}$ alkylthio, an aryl, or an aryl having at least one selected from the group consisting of a halogen, a $C_1$-$C_{18}$ alkyl, a halogenated $C_1$-$C_{18}$ alkyl, a $C_1$-$C_{18}$ alkyloxy, and a $C_1$-$C_{18}$ alkylthio.

An organic semiconductor device according to the present invention is an organic semiconductor device in which any one of the compound mentioned above is used.

The organic semiconductor device according to the present invention is preferably structured such that the organic semiconductor device is a thin film transistor having an organic semiconductor layer.

The organic semiconductor device according to the present invention is preferably structured such that the organic semiconductor device is a light emitting device having an organic carrier transfer layer and a light emitting layer.

The organic semiconductor device according to the present invention is preferably structured such that the organic semiconductor device has an electric field effect mobility of 0.1 cm²/Vs or higher.

The organic semiconductor device according to the present invention is preferably structured such that the organic semiconductor device has a ON/OFF current ratio of $10^5$ or greater.

A compound according to the present invention is a compound represented by General Formula:

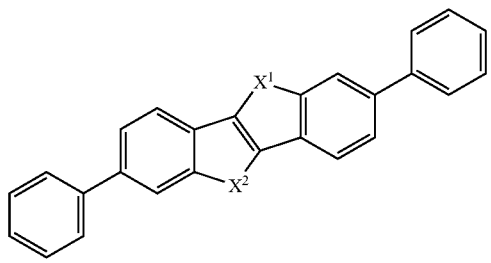

where $X_1$ and $X_2$ are independently a calcogen atom.

A compound according to the present invention is a compound represented by General Formula:

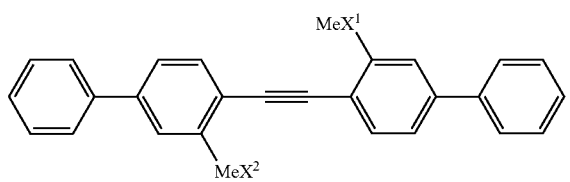

where $X_1$ and $X_2$ are independently a calcogen atom.

A method according to the present invention is a method of producing a compound, the method including:
adding iodine in a chloroform solution of a compound represented by:

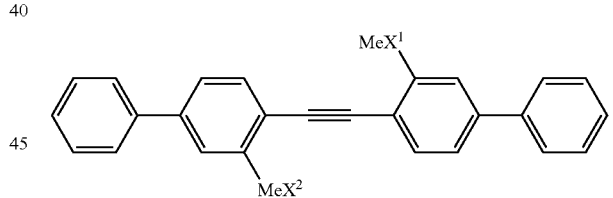

where $X_1$ and $X_2$ are independently a calcogen atom.

A method according to the present invention is a method of producing a compound, the method including:
adding powder of a calcogen atom to a BuLi/tBuOK solution of a compound represented by:

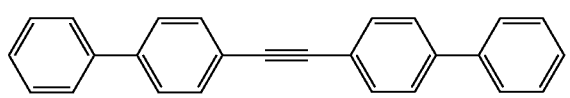

and
further adding methyl iodine therein.

A method according to the present invention is a method of producing a compound, the method including:
dropping ᵗBuLi into an anhydrous THF solution of a compound represented by:

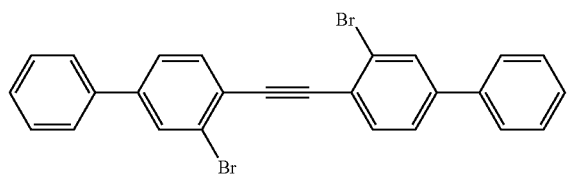

further adding powder of a calcogen atom therein; and further adding methyl iodine therein.

A method according to a method of producing a compound, the method using a reaction expressed as:

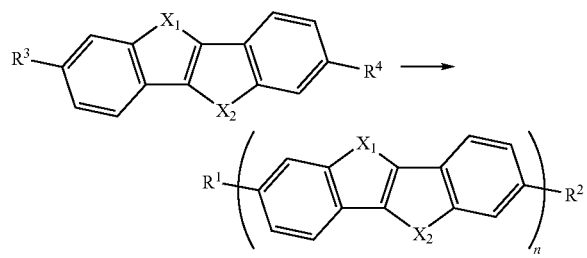

where $R^3$ and $R^4$ are independently a halogen, and $R^1$ and $R^2$ are independently an aryl having at least one selected from the group consisting of a halogen, a $C_1$-$C_{18}$ alkyl, a halogenated $C_1$-$C_{18}$ alkyl, a $C_1$-$C_{18}$ alkyloxy, and a $C_1$-$C_{18}$ alkylthio, and the reaction being a aryl-aryl cross-coupling reaction using the compound having $R^1$ and $R^2$.

A method according to the present invention is a method of producing a compound represented by Formula:

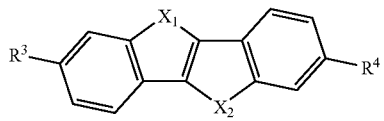

the method using a reaction expressed as:

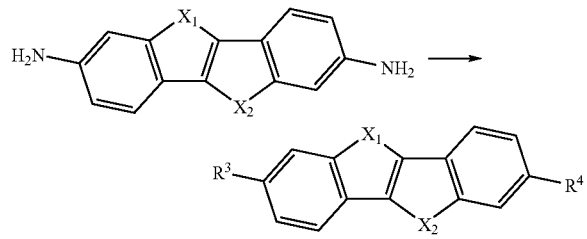

where $X^1$ and $X^2$ are independently a calcogen atom, and $R^3$ and $R^4$ are independently a halogen, and the reaction being proceeded with a metal halide having $R^3$ or $R^4$.

[Effect of the Invention]

The compound according to the present invention can be easily produced and has a relatively small molecular size, which enables easy formation of a thin film of the compound by the vapor deposition method or the like. By using the method according to the present invention for producing the compound, it is possible to obtain the compound according to the present invention by a small number of steps and with high yield. Moreover, the method according to the present invention can produce a synthetic product in which an amount of contaminants is little. Moreover, the method according to the present invention can utilize low-price raw materials and has a small number of steps, in each of which yields are high. Therefore, according to the present invention, an organic semiconductor device having excellent electric, electronic, and photoelectric properties can be produced more easily at a lower cost than conventional ones.

By using the compound according to the present invention in the device, it is possible to provide the device with a high electric field mobility. Moreover, the device in which the compound according to the present invention is used can operate in atmosphere without significant deterioration in its performance.

BRIEF DESCRIPTION OF DRAWINGS

FIG. 5 illustrates a driving stability test of a device, in which the device was switched on and off in atmosphere continuously 3000 times. The curves respectively represent one time driving, 2000-time driving, and 3000-time driving.

BEST MODE FOR CARRYING OUT THE INVENTION

Figure 1:
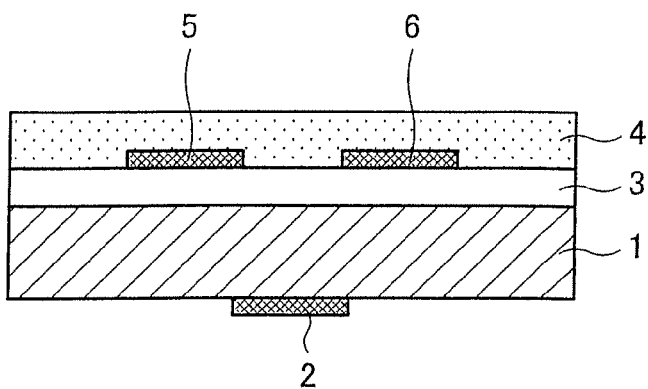
FIG. 1(a) is a cross sectional view of one embodiment of the present invention, schematically illustrating a structure of a thin film transistor.
FIG. 1(b) is a cross sectional view of one embodiment of the present invention, schematically illustrating a structure of a thin film transistor.
Figure 1:
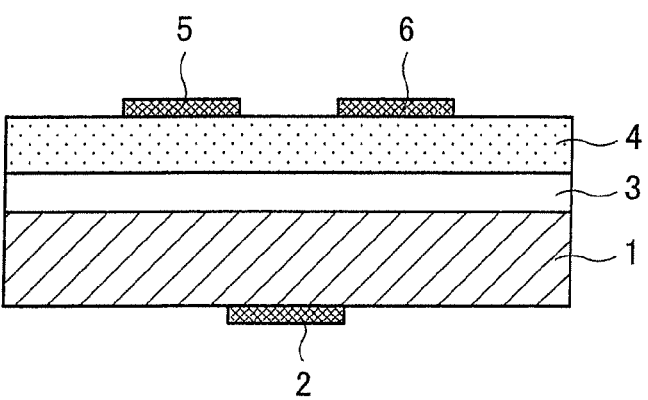

The inventors of the present invention have been studied on semiconductor properties of condensed polycyclic aromatic compounds having a heavy chalcogen atom (such as sulfur, selenium, or tellurium) based on a concept that an increase in intermolecular interaction in an organic thin film device is effective in improving a carrier mobility therein. The calcogen atom having a large atomic radius causes intermolecular collision. Thus, condensed polycyclic aromatic compounds having the heavy chalcogen atom is more effective in enhancing the intermolecular interaction than a condensed polycyclic aromatic compounds constituted of hydrocarbon. As a result of the study, the inventors of the present invention found that selenium analogous of a benzochalcogenophene derivative had a very high electric field effect mobility. Further diligent studies of the inventors on this finding accomplished the present invention.

A condensed polycyclic aromatic compound according to the present invention and a method of producing the same are described in the followings, referring to chemical formulae below.

The present invention provides [benzochalcogeno[3,2-b][1]benzochalcogenophene derivative, which is a condensed polycyclic aromatic compound represented by:

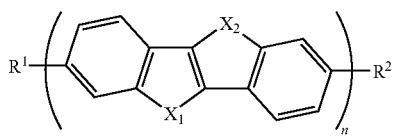

where $X^1$ and $X^2$ are independently a calcogen atom, and n is an integer in a range of 1 to 3. In the present DESCRIPTION, the "calcogen atom" may be oxygen, sulfur, selenium, or tellurium, and is preferably sulfur, selenium, or tellurium.

In preferable embodiments, a condensed polycyclic aromatic compound according to the present invention is arranged such that $R^1$ and $R^2$ are independently a halogen, a $C_1$-$C_{18}$ alkyl, a halogenated $C_1$-$C_{18}$ alkyl, a $C_1$-$C_{18}$ alkyloxy, a $C_1$-$C_{18}$ alkylthio, an aryl, or an aryl having at least one selected from the group consisting of a halogen, a $C_1$-$C_{18}$ alkyl, a halogenated $C_1$-$C_{18}$ alkyl, a $C_1$-$C_{18}$ alkyloxy, and a $C_1$-$C_{18}$ alkylthio. Examples of the aryl group encompass phenyl group, naphtyl group, anthranil group, furyl group, thienyl, selenofuryl group, thienothienyl group, etc. In more preferable embodiments, a condensed polycyclic aromatic compound according to the present invention is arranged such that $R^1$ and $R^2$ are independently a compound having at least one of a halogen, a $C_1$-$C_{18}$ alkyl, a halogenated $C_1$-$C_{18}$ alkyl, a $C_1$-$C_{18}$ alkyloxy, a $C_1$-$C_{18}$ alkylthio, and an aryl, and are represented by:

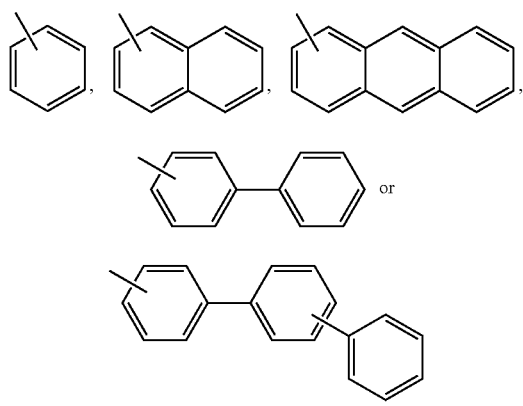

The present invention further provides a method of producing the condensed polycyclic aromatic compound. The method according to the present invention for producing the compound preferably uses the following reaction represented by Reaction Formula:

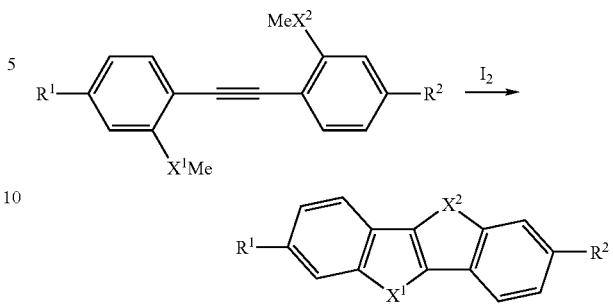

where $X^1$ and $X^2$ are independently a calcogen atom, and $R^1$ and $R^2$ are independently a halogen, a $C_1$-$C_{18}$ alkyl, a halogenated $C_1$-$C_{18}$ alkyl, a $C_1$-$C_{18}$ alkyloxy, a $C_1$-$C_{18}$ alkylthio, an aryl, or an aryl having at least one selected from the group consisting of a halogen, a $C_1$-$C_{18}$ alkyl, a halogenated $C_1$-$C_{18}$ alkyl, a $C_1$-$C_{18}$ alkyloxy, and a $C_1$-$C_{18}$ alkylthio.

The inventors of the present invention tried to obtain the compounds according to the present invention by a synthesis method described in "the synthesis of the unsubstituted compound": Sashida, H. and Yasuike, S. J. Heterocyclic Chem. 35, 725-726 (1988). The synthesis method is as follows:

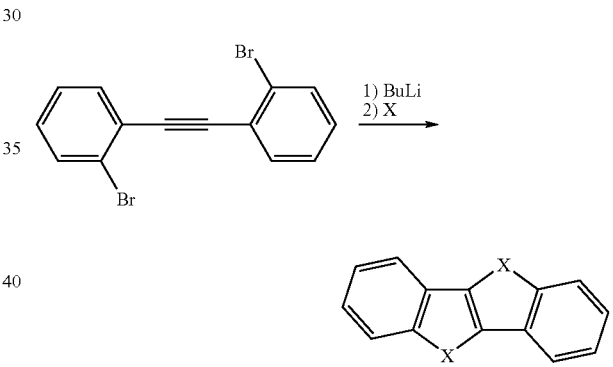

This attempt could synthesize only a compounds represented by:

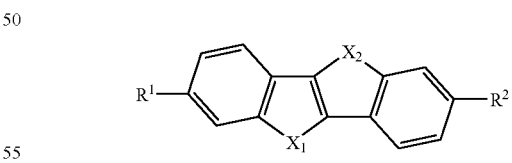

where $R^1$=$R^2$=H. Therefore, the condensed polycyclic aromatic compound is a novel compound that never be attained by a conventional method.

In the first embodiment, a condensed polycyclic aromatic compound 3 according to the present invention is synthesized by performing a reaction according to Reaction Formula (1), so as to synthesize a novel compound 2; and performing reaction according to Reaction Formula (2). The compound 3 is represented by:

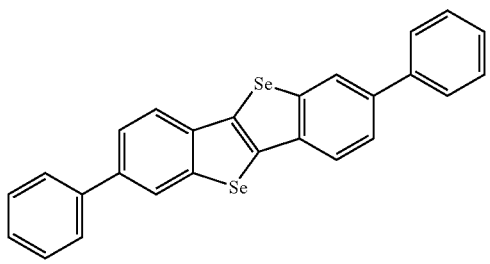

Reaction Formula (1) is expressed as:

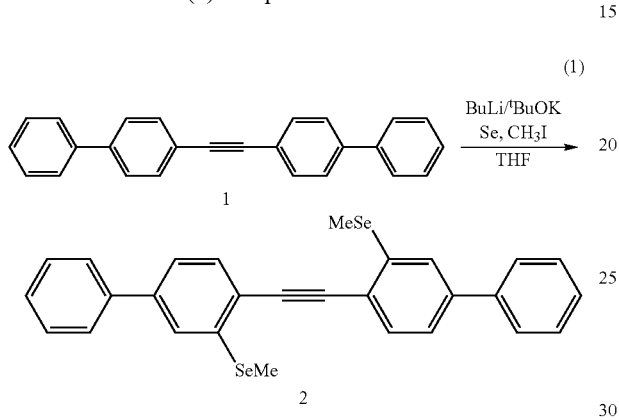

The compound 2 is represented by:

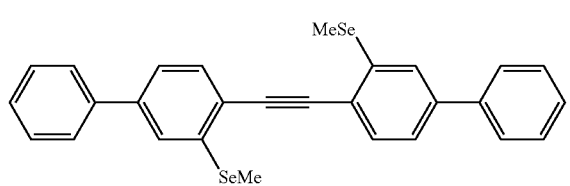

Reaction Formula (2) is expressed as:

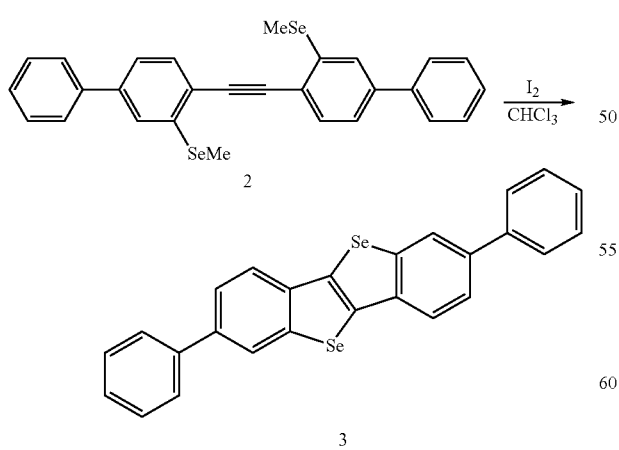

A compound 1 is a well known material and can be easily synthesized from commercially available compounds by a well known method.

The inventors of the present invention tried to synthesize the compound 3 from the compound 1 directly, only to fail.

The reaction (reaction formula (2)) syntheses the compound 3 from the compound 2 by breaking C—Se bonding in methyl selenide (MeSe). It has been known that C—Se bonding is very strong. Thus, it was utterly unexpected that this reaction would proceed. The inventors of the present invention successfully proceeded this reaction by carrying out this reaction with a greater amount of iodine and heat application on the reaction liquid.

The first embodiment is described referring to the example where the condensed polycyclic aromatic compound represented by:

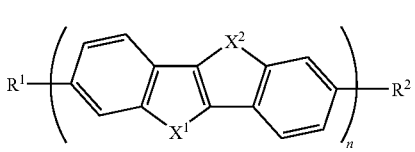

is [1]benzochalcogeno[3,2-b][1]benzochalcogenophene derivative where $R^1=R^2$=phenyl, $X^1=X^2$=Se, and n=1. Reading this DESCRIPTION, a person skilled in the art will easily understand that the condensed polycyclic aromatic compound according to the present invention is not limited to this example and a desired condensed polycyclic aromatic compound can be obtained by appropriately selecting starting materials.

Moreover, it is necessary in Reaction Formula (1) that the compound 1 and the base (nBuLi/tBuOK) be mixed at an extremely low temperature and then the temperature is increased to proceed abstraction of ortho-hydrogen. The mixing temperature of the compound 1 and the base (nBuLi/$^t$BuOK) is preferably in a range of −100 to −60° C., and more preferably in a range of −70 to −80° C. The temperature for proceeding the ortho-hydrogen abstraction is preferably in a range of −30 to 0° C., and more preferably in a range of −30 to −20° C.

Moreover, Reaction Formula (2) may use a halogen (bromine, chloride, mixed-halogen compound, iodine chloride) other than iodine may be used similarly. Examples of the solvent usable in Reaction Formula (2) is a chlorine-based solvent whose boiling point is relatively high (approximately 70° C. or higher).

In a second embodiment, a condensed polycyclic aromatic compound 3 according to the present invention being represented by:

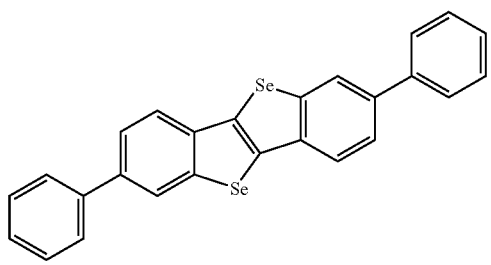

is synthesized via a synthetic pathway involving no Reaction Formula (1). Preferably, the present embodiment is arranged such that the compound 2 from which the compound 3 is prepared, is synthesized from another well known compound 4 represented by:

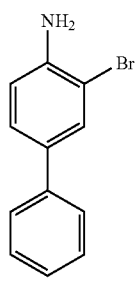

More specifically, the compound 3 can be synthesized by proceeding a reaction according Reaction Formula (3) expressed as:

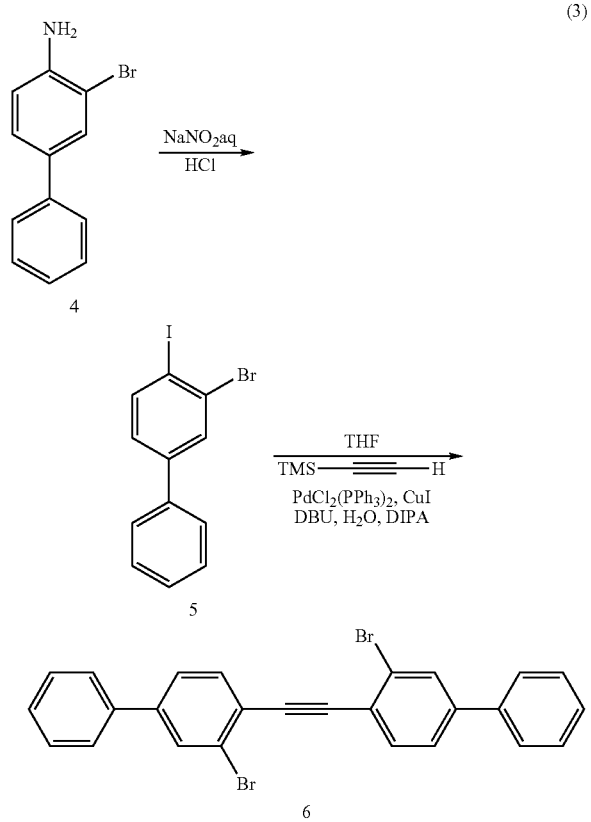

(3)

so as to synthesize a novel compound 6, and proceeding a reaction according to Reaction Formula (4) expressed as:

(4)

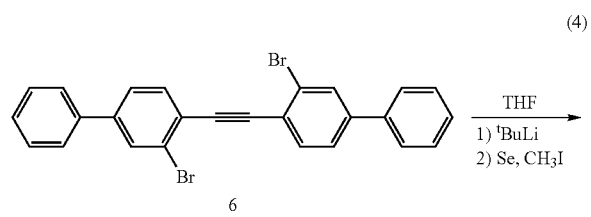

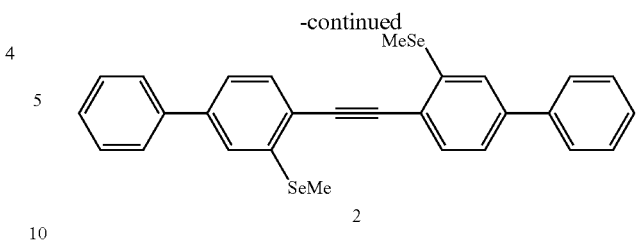

The compound 4 is a well known material and can be easily synthesized from commercially available compounds by a well known method.

The inventors of the present invention tried to synthesize the compound 1 from a compound 6 obtained in Reaction Formula (3) directly, without preparing an intermediate compound 2. This attempt was not successful.

The second embodiment is described referring to the example where the condensed polycyclic aromatic compound represented by:

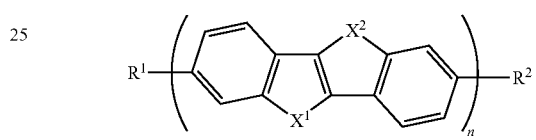

is [1]benzochalcogeno[3,2-b][1]benzochalcogenophene derivative where $R^1=R^2=$phenyl, $X^1=X^2=$Se, and n=1. Reading this DESCRIPTION, a person skilled in the art will easily understand that the condensed polycyclic aromatic compound according to the present invention is not limited to this example and a desired condensed polycyclic aromatic compound can be obtained by appropriately selecting agents used in Reaction Formulae (3) and (4).

It was found that the novel synthetic method via Reaction Formula (2) as described in the first and second embodiments produces the compound without much impurity therein. Therefore, the synthetic method makes it possible to easily produce the [1]benzochalcogeno[3,2-b][1]benzochalcogenophene derivative. Moreover, the [1]benzochalcogeno[3, 2-b][1]benzochalcogenophene derivative thus produced by the synthetic method is such a relatively small molecule that can easily form an organic semiconductor thin film by a vapor deposition method or the like.

In the present DESCRIPTION, the term "thin film" is a film that is preferably as thin as possible. A preferable thin film for use in an organic semiconductor is in a range of 1 nm to 1 μm, preferably in a range of 5 to 500 nm, more preferably 10 to 500 nm in thickness.

Furthermore, a high electric field effect mobility was observed in a device in which the [1]benzochalcogeno[3,2-b][1]benzochalcogenophene derivative was used. Specifically, the device showed an electric field effect mobility exceeding 0.1 cm$^2$/Vs, reaching 0.31 cm$^2$/Vs at maximum.

Surprisingly, the device in which the [1]benzochalcogeno[3,2-b][1]benzochalcogenophene derivative was used showed no significant deterioration in its performance when it was operated in the atmosphere. Furthermore, even after it was stored in a normal method for 2-month time after being produced, the 2-month storage did not deteriorate the performance of the device at all so that the device could reproduce its initial performance either in vacuum or in atmosphere.

In a third embodiment, a condensed polycyclic aromatic compound 3 according to the present invention represented by:

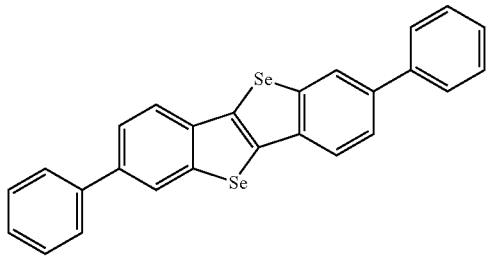

is synthesized via a synthetic pathway involving none of reaction formulae (1) to (4). In the present embodiment, a compound 3 is synthesized from a compound 7 according to Reaction Formula (5), the compound 7 being represented by:

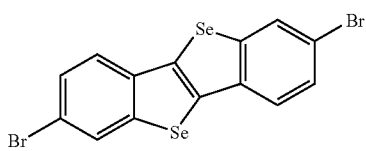

7 and Reaction Formula (5) being represented by:

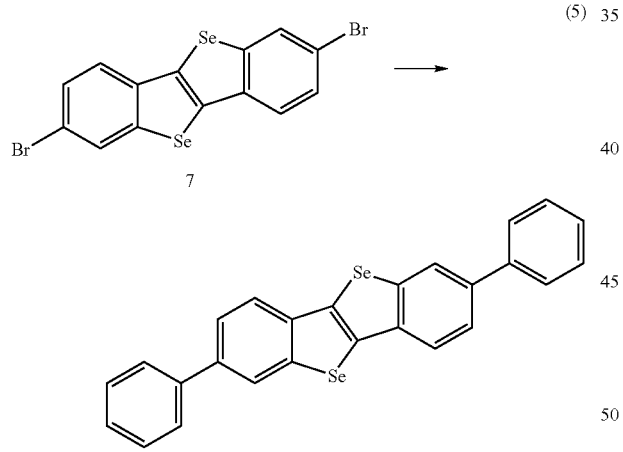

(5)

3

The compound 7 is synthesized from a well know compound 8 or 9, the compound 8 being represented by:

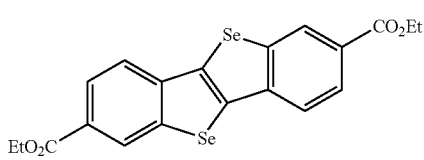

8 and the compound 9 being represented by:

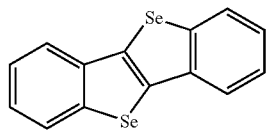

9

That is, the compound 7 can be synthesized by selective halogenation (bromination in the present embodiment) at the 2, 7 positions.

The compound 9 may be synthesized from a commercially available compound directly or indirectly via a compound 10. The commercially available compound is represented by:

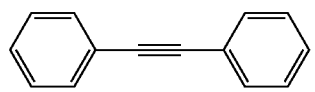

The compound 10 is represented by:

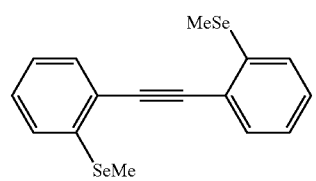

10

Moreover, the compound 9 may be synthesized via an intermediate compound from a commercially available compound being represented by:

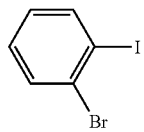

The intermediate compound is represented by:

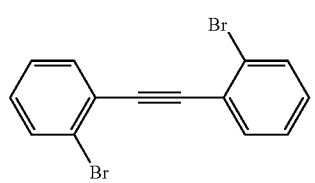

The third embodiment is described referring to the example where the condensed polycyclic aromatic compound represented by:

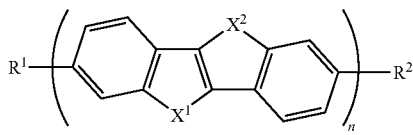

is [1]benzochalcogeno[3,2-b][1]benzochalcogenophene derivative where $R^1=R^2$=phenyl, $X^1=X^2$=Se, and n=1. Reading this DESCRIPTION, a person skilled in the art will easily understand that the condensed polycyclic aromatic compound according to the present invention is not limited to this example and a desired condensed polycyclic aromatic compound can be obtained by using another chalcogen in replacement of Se in the synthesis of the intermediate compound 9 or appropriately selecting an agent used in Reaction Formula (5). The reaction in Reaction Formula (5) should be an aryl-aryl cross-coupling reaction catalyzed by a transition metal catalyst. For example, the reaction in reaction formula (5) may be Suzuki cross-coupling (organic boron reagent, Ar—B(OH)$_2$ or Ar—B(OR)$_2$), Stille cross-coupling (organic tin reagent, Ar—SnR$_3$, (where R is an alkyl group such as methyl, n-butyl or the like)), Kumada cross-coupling (organic magnesium reagent, ArMgX (where X is chlorine, bromine, or iodine)).

In the present DESCRIPTION, what is meant by the transition metal catalyst is a transition metal element and a transition metal compound having a transition metal element itself and a ligand of various kinds coordinated thereto. More specifically, the transition metal catalyst may be, not limited to, palladium, nickel, titanium, iron, platinum, gold, or copper. The ligand may be, but not limited to, a phosphine compound, an amine compound, a nitrile compound, a halogen, or carbonyl compound. Preferable metals are palladium and nickel, and preferable ligands are triphenylphosphine, bis(diphenylphosphino)ferrocene, bis(diphenylphosphino)propane. Most preferable catalysts are tetrakis(triphenylphosphine)palladium, dichlorodiphenylphosphinoferrocenepalladium, dichlorobis(diphenylphosphine)propanenickel. Albeit the present embodiment is described referring to the example in which low-priced and easily available tetrakis(triphenylphosphino)palladium is used, the catalyst is not limited to this. The use of tetrakis(tripenylphosphine) as the catalyst as in the present embodiment is especially preferable due to its low price and easy availability.

The reaction solvent for use in the coupling reaction can be selected from various solvents such as ether solvents (diethyl ether, tetrahydrofuran (THF), dioxane, dimethoxyethane (DME), etc.), aprotic polar solvents (N,N-dimethylformamide (DMF), N,N-dimethylacetoamide (DMA), N,N-dimethylimidazolidinon (DMI), dimethylsulfoxide (DMSO), N-methylpyrrolidone (NMP), etc.), carbohydrate solvents (toluene, xylene, etc.), aromatic solvent (chlorobenzene, benzonitrile, etc.), and other solvents, considering which kind of the coupling reaction is to take place. Albeit the following Examples discuss a reaction using N,N-dimethylformamide (DMF) by way of example, the present invention is not limited to this.

In the fourth embodiment, a condensed polycyclic aromatic compound 3 according to the present invention represented by:

is synthesized from the compound 9 via a synthetic pathway similar to the synthetic pathway described in the third embodiment, but is different from the third embodiment in that the compound 2, from which the compound 9 is synthesized, is synthesized via a different synthetic pathway from the synthetic pathway adopted in the third embodiment.

That is, in the present embodiment, the unsubstituted compound 9 is synthesized by proceeding a reaction starting from a compound 10 by Reaction Formula (8) so as to form a compound 14, and by proceeding a reaction according to Reaction Formula (9). Reaction formula (8) is represented by:

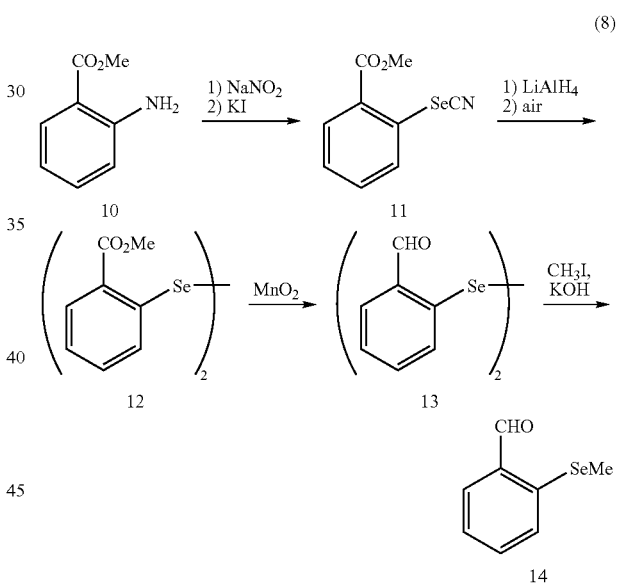

And Reaction Formula (9) is represented by:

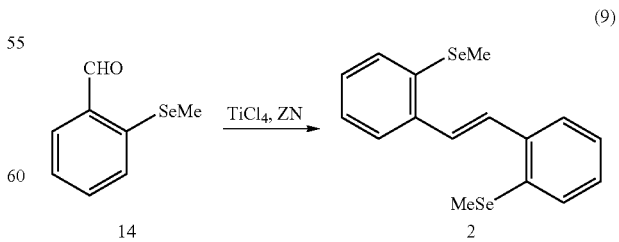

The compound 10 may be a commercially available reagent or may be synthesized from a commercially available reagent.

The synthetic method in the present embodiment is preferably suitable for mass synthesis, because the raw materials are inexpensive, and the synthetic method is a combination of the reactions suitable for attaining large reaction systems.

The reaction pathway from the compound 10 to the compound 14, that is, the reaction shown by the reaction formula (8) may be carried out by appropriately adopting reaction conditions described in M. Iwaoka et al., J. Am. Chem. Soc. 2004, 126, 5309-5317.

The fourth embodiment is described referring to the example where the condensed polycyclic aromatic compound represented by:

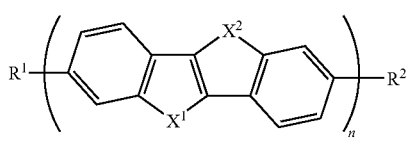

is [1]benzochalcogeno[3,2-b][1]benzochalcogenophene derivative where $R^1=R^2$=phenyl, $X^1=X^2$=Se, and n=1. Reading this DESCRIPTION, a person skilled in the art will easily understand that the condensed polycyclic aromatic compound according to the present invention is not limited to this example and a desired condensed polycyclic aromatic compound can be obtained by using another chalcogen in replacement of Se in the synthesis of the intermediate compound 9 or appropriately selecting an agent used in Reaction Formula (5), as described in the third embodiment. The reaction of Reaction Formula (5) is as described above.

Moreover, the inventors of the present invention contrived a more efficient method of producing a compound according to the present invention. This method is described in the fifth embodiment below.

In the fifth embodiment, the condensed polycyclic aromatic compound 16 according to the present invention represented by:

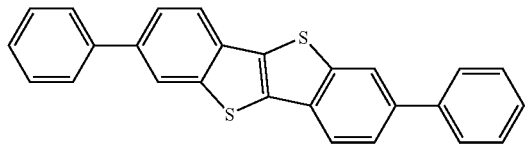

is synthesized from a later-described compound 20 via a compound 21.

One example of the production method is a method including synthesizing a dinitro derivative (compound 19) of benzothieno[3,2-b]benzothiophine from a later-described compound 17, synthesizing a diamino derivative (compound 20) of the compound thus synthesized, substituting amino groups of the diamino compound with a halogen so as to obtained dihalogen derivative (compound 21), performing the cross-coupling method as described in the third embodiment, so as to obtained a compound 16.

More specifically, in the present embodiment, a compound 20 (diamino derivative) is synthesized, starting from a compound 17, via a 4-step reaction expressed as Reaction Formula (10):

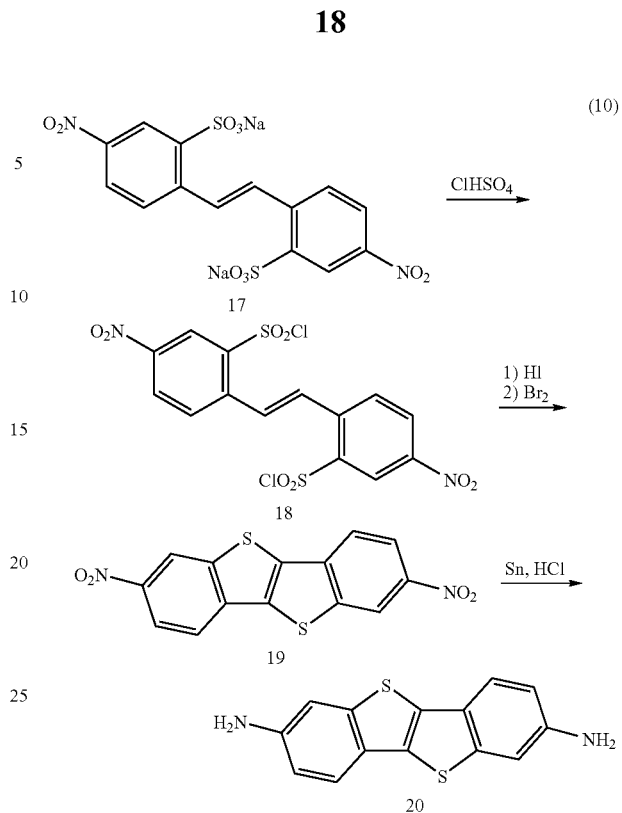

Then, to convert the compound 20 to a diazonium salt, the compound 20 undergoes a reaction expressed as Reaction Formula (11):

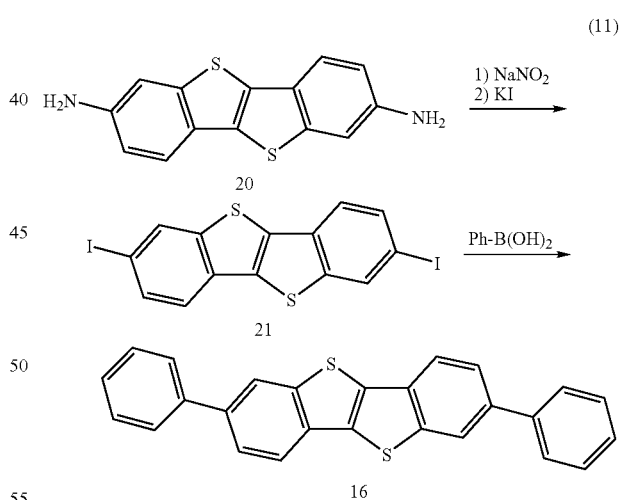

After that, the diazonium salt is converted to 2,7-diiodo derivative (compound 21). In the above, the reagent for use in the diazotization may be a nitride compound such as sodium nitrite, isoamyl nitrite, t-butyl nitrite, etc. For low cost and easy availability, sodium nitrite and isoamyl nitrite are preferable. Albeit the later-descried Examples discusses a reaction using sodium nitrite, a person skilled in the art will easily understand that the reagent for the diazotization is not limited to sodium nitrite. A reaction temperature of diazotization is preferably low in range of 25° C. to −20° C., especially preferably in a range of 0° C. to 5° C. For the conversion of the diazonium salt to the compound 21, water-soluble iodide may be used as the reagent. Among iodides, lithium iodide, sodium iodide, potassium iodide, and cesium iodide can be used preferably. For low cost and easy availability, potassium iodide is especially suitable. In order to complete iodination, the reaction should be carried out with heating or for a long time. The reaction temperature is 80° C. or higher, preferably at a reflux temperature (100° C.). Moreover, the reaction time is in a range of 30 minutes to 24 hours. In order to secure the completion of the reaction, the reaction time is preferably 2 hours or longer. In the Examples, the reaction is terminated after 3 hour reflux. However, the condition is not limited to this.

The compound 16 can be synthesized by carrying out coupling reaction after the halogenation. The coupling reaction may be with phenylboronic acid in the presence of palladium catalyst or the like, for example. The compound 17 may be a commercially available reagent or may be synthesized from a commercially available reagent easily. The coupling reaction may be carried out under various conditions, as described in the third embodiment for Reaction Formula (5).

The preparation of the compound 20 from the compound 17 may be carried out in any way, and may be performed under reaction conditions described in S. Y. Zherdeva et al., Zh. Organi. Khimi, 1980, 16, 430-438.

The fifth embodiment is described referring to the example where the condensed polycyclic aromatic compound represented by:

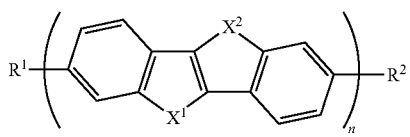

is [1]benzochalcogeno[3,2-b][1]benzochalcogenophene derivative where $R^1=R^2$=phenyl, $X^1=X^2$=S, and n=1. The condensed polycyclic aromatic compound according to the present invention is not limited to this example. For example, reading this DESCRIPTION, a person skilled in the art will easily understand that a desired condensed polycyclic aromatic compound can be obtained by selecting an appropriate regent for use in Reaction Formula (11). The reaction to obtain the compound 16 from the compound 21 in Reaction Formula (11) should be an aryl-aryl cross-coupling reaction catalyzed by a transition metal catalyst. For example, the reaction of Reaction Formula (5) may be Suzuki cross-coupling (organic boron reagent, Ar—B(OH)$_2$ or Ar—B(OR)$_2$), Stille cross-coupling (organic tin reagent, Ar—SnR$_3$, (where R is an alkyl group such as methyl, n-butyl or the like)), Kumada cross-coupling (organic magnesium reagent, ArMgX (where X is chlorine, bromine, or iodine)).

The compound 16 is obtained by carrying out aryl-aryl cross-coupling reaction with a dihalogen derivative obtained by substituting iodine in the compound 21 with another halogen. For example, the synthesis (Reaction Formula (11)) of the compound 21 via the diazotization of the compound 20 may be carried out with CuBr (copper bromide) instead of KI (potassium iodide). By this, a bromine derivative of the compound 21 is obtained, in which bromide substitutes iodine. Such derivatives in which a halogen is introduced are applicable to the preparation of the compound 16 via the reaction expressed as Reaction Formula (11).

Figure 6:
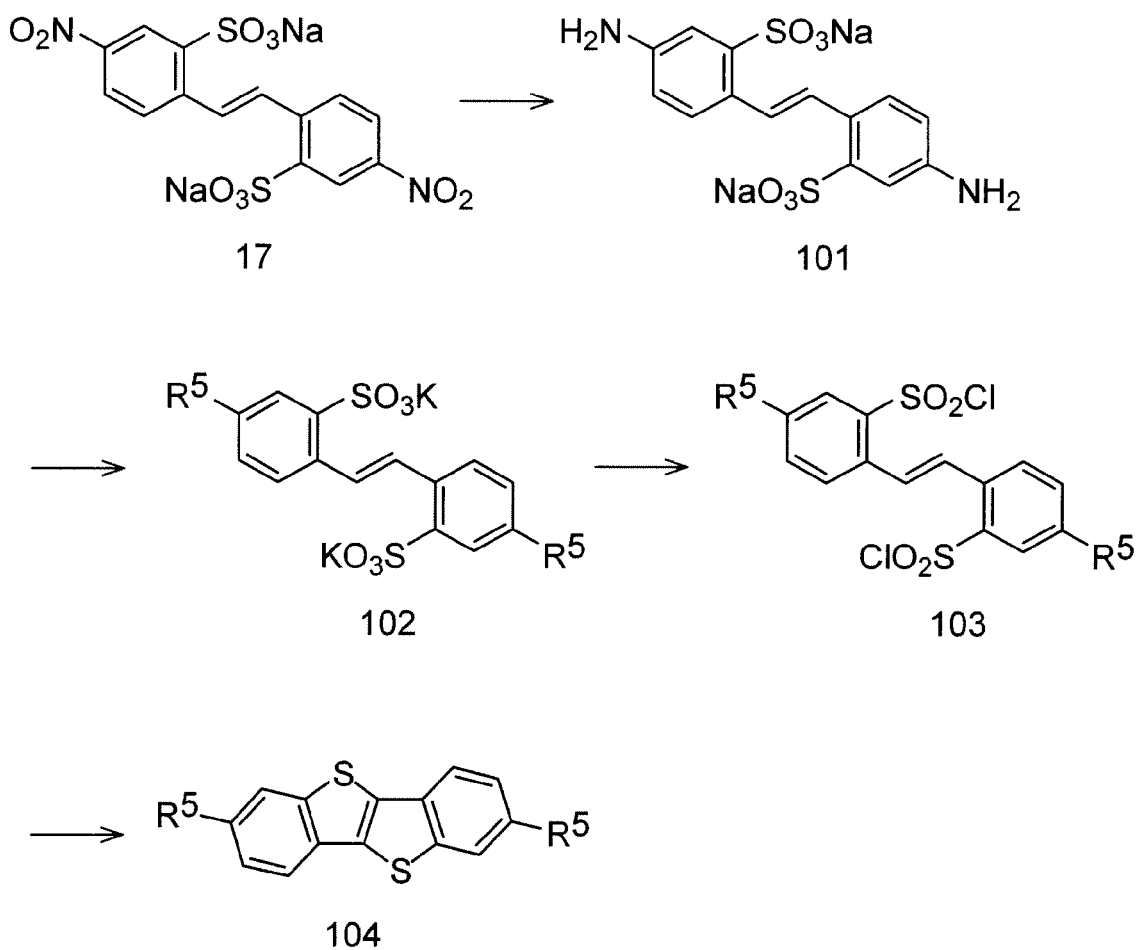
FIG. 6 is a screen illustrating reaction steps in one embodiment of the present invention.

Moreover, the preparation of dibromo derivative or dichloro derivative of benzothieno[3,2-b]benzothiophene from the compound 17 is not limited to the method shown in Reaction Formula (10). That is, a method as illustrated in FIG. 6 is also applicable, in which a compound 103 is obtained from the compound 17 and then a halogen derivative of benzothieno[3,2-b]benzothiophene is obtained. More specifically, the method illustrated in FIG. 6 is as follows. Firstly, a compound 101 is obtained from the compound 17 by using 1% ammonium chloride solution containing iron powder. Then, a compound 102 is obtained by Sandmeyer reaction, which is a known method. From the compound 102, the compound 103 is obtained using phosphorus pentachloride. After sulfonyl chloride group of the compound 103 is selectively reduced to thiol group, double bonds of the compound 103 undergo addition-dehydrogenation thereby converting the compound 103 to a compound 104.

Any stage of the reaction illustrated in FIG. 6 may be carried out with a reducing agent of various kinds (which may be, but not limited to, sodium boron hydride, aluminum-Lithium hydride, zinc, tin, iron, hydriodic acid, or the like), and dehydrogenating agent (which may be, but not limited to, lead tetraacetate, a quinone derivative of a various kind, a chromate, manganese dioxide, bromide, chloride, or the like). All the reagents mentioned here by way of example are preferable because of their high reactivity, relatively low price, and easy availability. It is especially preferable to obtain the compound 104 by using hydriodic acid as the reducing agent and bromide as the oxidizing agent, because the use of these reagents does not require isolation and refinement in the first reduction stage, and will not produce a by-product at the addition-dehydrogenation.

In FIG. 6, $R^5$ is Cl or Br. The compound 16 can be synthesized by using the thus obtained compound 104 instead of the compound 21 in Reaction Formula (11). The method illustrated in FIG. 16 may be carried out under reaction conditions described in S. Y. Zherdeva et al., Zh. Organi. Khimi, 1980, 16, 430-438.

However, iodine is generally and advantageous over bromide in the aryl-aryl cross-coupling reaction (Reaction Formula (11)) in the present of a transition metal catalyst, because iodine is more reactive than bromide in the aryl-aryl cross-coupling reaction.

Next, a device including the organic semiconductor material made of the condensed polycyclic aromatic compound according the present invention is described referring to FIGS. 1(a) and 1(b).

FIGS. 1(a) and 1(b) respectively schematic cross sectional views of thin film transistor devices, illustrating embodiments of the present invention.

In FIG. 1(a), an organic semiconductor device 10 according to the present invention includes a contact metal 2 on a surface of a substrate 1 that acts as a gate electrode. On a surface of the substrate 1 opposite to the contact metal 2, a dielectric layer 3 is provided. Provided on the dielectric layer 3 are a source 5 and a drain 6, and contact channels respectively for the source 5 and drain 6. Furthermore, an organic semiconductor material 4 is deposited thereon.

In FIG. 1(b), an organic semiconductor device 11 according to the present invention includes a contact metal 2 on a surface of a substrate 1 that acts as a gate electrode. On a surface of the substrate 1 opposite to the contact metal 2, a dielectric layer 3 and an organic semiconductor material 4 are provided. Provided on the organic semiconductor material 4 are a source 5 and a drain 6, and contact channels respectively for the source 5 and drain 6.

The substrate 1 may be p type or n-type but is preferably n-doped for the sake of its function as the gate electrode. Moreover, the substrate 1 may be, for example: a ceramic substrate made of glass, quartz, aluminum oxide, sapphire, silicon nitride, silicon carbide, or the like; a semiconductor substrate made of silicon, germanium, gallium arsenic, gallium phosphide, gallium nitride, or the like; a resin substrate made of polyester (such as polyethyleneterephthalate, polynaphthaleneterephthalate), polyethylene, polypropylene, polyvinylalcohol, ethylenevinylalcohol copolymer, cyclic polyolefine, polyimide, polyamide, polystylene, or the like; paper; nonwoven fabric; or the other material. Silicon is preferable.

The contact metal 2 is preferably, but not limited to, gold, platinum, silver, copper, aluminum, nickel, titanium, chrome, magnesium-silver, organic conductive compound, or calcium. For easy handling, the contact metal 2 is preferably gold or silver. When the substrate 1 is made of silicone, the ferroelectric layer 3 is made of silicone dioxide. Thermal oxidation is preferably adopted to form the ferroelectric layer 3 on the substrate 1. Moreover, examples of means for forming the connect channels of the source 5 and the drain 6 encompass electron lithography, photolithography, shadow masking, silk screen method, and the like. However, the present invention is not limited to these. Preferably, the contact channel is formed by shadow masking method, electron lithography, or photo lithography.

The deposition of the organic semiconductor material 4 may be carried out by a dry film formation method such as vacuum deposition method, CVD method, sputtering method, laser vapor deposition method, or a wet film formation in which a thin film is formed by removing a solvent or dispersion medium after a solution or dispersion solution is applied on the substrate. However, the deposition of the organic semiconductor material 4 is not limited to these. Preferably, the organic semiconductor material 4 is deposited by vacuum deposition. In case where vacuum deposition is adopted, the pressure is preferably $10^{-1}$ Pa or lower, and more preferably $10^{-3}$ Pa or lower.

Here, the organic semiconductor materials generally have a high tendency to be p type (hole transporting type). Therefore, there have been many excellent p-type organic semiconductor materials. On the other hand, there are only few types of n-type (electron transporting type) materials, and the n-type materials are poorer in performance than the p type materials. Thus, there are very large demand for development of an n-type organic semiconductor material and a method of manufacturing the same.

One effective practical means for developing an n-type organic semiconductor material is to convert the polarity from p type to n-type by introducing an electron-attracting substituent in the p type organic semiconductor material. For such a polarity conversion, a plural kinds of substituents having cyano, fluorine, or the like are preferably usable. That is, a person skilled in the art can convert a generally p type organic semiconductor material to n-type.

As described above, the present invention provides a device including an organic semiconductor layer made of [1]benzochalcogeno[3,2-b][1]benzochalcogenophene derivative, which is a condensed polycyclic aromatic compound represented by:

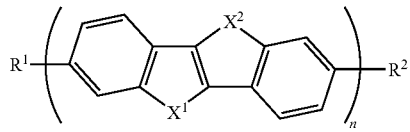

where $X^1$ and $X^2$ are independently a calcogen atom, n is an integer in a range of 1 to 3, and $R^1$ and $R^2$ are independently a halogen, a $C_1$-$C_{18}$ alkyl, a halogenated $C_1$-$C_{18}$ alkyl, a $C_1$-$C_{18}$ alkyloxy, a $C_1$-$C_{18}$ alkylthio, an aryl, or an aryl having at least one selected from the group consisting of a halogen, a $C_1$-$C_{18}$ alkyl, a halogenated $C_1$-$C_{18}$ alkyl, a $C_1$-$C_{18}$ alkyloxy, and a $C_1$-$C_{18}$ alkylthio.

In the condensed polycyclic aromatic compound according to the present invention, it is more preferable that $R^1$ and $R^2$ be independently a halogenated $C_1$-$C_{18}$ alkyl, a $C_1$-$C_{18}$ alkyloxy, a $C_1$-$C_{18}$ alkylthio, an aryl, or an aryl having at least one selected from the group consisting of a halogen, a $C_1$-$C_{18}$ alkyl, a halogenated $C_1$-$C_{18}$ alkyl, a $C_1$-$C_{18}$ alkyloxy, and a $C_1$-$C_{18}$ alkylthio.

In the condensed polycyclic aromatic compound according to the present invention, it is especially preferable that at least one of $R^1$ and $R^2$ be the aryl, and it is further preferable that $R^1$ and $R^2$ be the aryl.

The condensed polycyclic aromatic compound according to the present invention having the aryl are especially excellent in the electric field mobility and On/Off current ratio, and therefore especially preferable as an organic semiconductor.

Examples of applications of the organic semiconductor device according to the present invention having such a structure encompass diodes, thin film transistors, memories, photodiodes, light emitting diodes, light emitting transistors, gas sensors, bio sensors, blood sensors, immunosensors, artificial retina, taste sensors, etc. It is preferable that the organic semiconductor device according to the present invention function as a thin film transistor or light emitting device. Preferable applications of such a thin film transistor encompass transistors for switching pixels constituting a display, signal driver circuit elements, memory circuit elements, signal processing circuit elements, etc. Examples of the display are liquid crystal display, dispersed type liquid crystal display, electrophoresis display, particle-rotation-type display device, electro chromic display, organic electroluminecence display, electronic paper, etc.

More specifically, the organic semiconductor device preferably has an electric field effect mobility of 0.1 cm²/Vs or higher. The organic semiconductor device may have a ON/OFF current ratio of $10^5$ or greater. Such an organic semiconductor device is very useful as a thin film transistor, or a light emitting device having an organic carrier transport layer or light emitting layer. Further, an organic semiconductor device according to the present invention is advantageous not only in its high electric field mobility but also in its ability of operating in the atmosphere with no significant deterioration in its performance.

As described above, an object of the present invention is to provide a novel condensed polycyclic aromatic compound that satisfies both a high electric field effect mobility and high On/Off current ratio, which are required for an organic semiconductor material, and to provide an organic semiconductor device having a good performance by using the condensed polycyclic aromatic compound.

The present invention is described in more details referring to the following Examples, which are not to limit the present invention.

EXAMPLES

Example 1

Synthesis of Bis(4-biphenyl-il)acetylene (Compound 1)

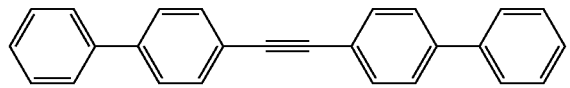

4-bromobiphenyl (5.0 g, 20 mmol) was dissolved in a mixture solvent of diisoprophylamine (40 mL)-benzoic anhydride (20 mL) under nitrogen atmosphere and then deaerated. In the solution thus prepared, trimethylsilylacetylene, (1.4 mL, 10 mmol), chlorobis(triphenylphosphine) palladium (0.84 g, 1.2 mmol), cuprous iodide (0.38 g, 2.0 mmol), diazabicycloundecene (DBU, 1.83 g, 0.94 mmol) and water (0.14 mL, 7.8 mmol) were added and stirred at 60° C. for 18 hours. The reaction completed, thereby precipitating a solid. After water (50 mL) was added thereto, the solid was filtered out. Then, the solid was washed with water, methanol, and hot hexane, and then dried under vacuum. The thus prepared solid was extracted with carbon disulfide and recrystallized, thereby obtaining a color-less plate-like crystal of bis(4-biphenyl-il)acetylene (Compound 1) of 1.01 g with a yield of 31%.

Melting Point: 256 to 258° C. (Literature value in Nakasuji, K. et al. Bull. Chem. Soc. Jpn. 45, 883-891 (1972): mp. 253 to 254° C.)

$^1$H NMR (400 MHz, CDCl$_3$) δ 7.64 to 7.59 (m, 12H), 7.46 (t, J=7.6 Hz, 4H), 7.44 (tt, J=1.2 Hz, J=7.6 Hz, 2H)

$^{13}$C NMR (100 MHz, CDCl$_3$) δ 140.97, 140.34, 132.02, 128.86, 127.63, 127.02, 122.19, 89.98

MS (EI, 70 eV) m/z=330 (M$^+$)

Example 2

Synthesis of bis(3-selenomethyl-4-biphenyl-il)acetylene (compound 2)

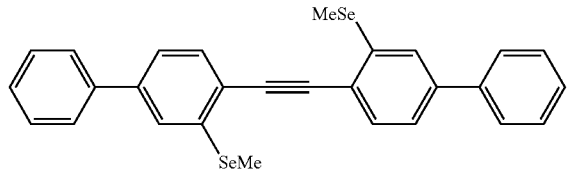

Into 3-necked 50 mL flask, potassium t-butoxide (0.89 g, 8.0 mmol), THF (15 mL) were added and cooled to −78° C. under nitrogen atmosphere. Then, 5.1 mL (8.0 mmol) of n-butyllithium-hexane solution of 1.54M was gradually dropped and then stirred for 10 min. After that, bis (4-biphenyl-il)acetylene (Compound 1) (1.0 g, 3.0 mmol) obtained in Example 1 was further added therein. The thus prepared reaction solution was stirred at −78° C. for 30 min, and then the temperature thereof was gradually increased to −30° C. Subsequently, the reaction solution was stirred at this temperature for 1.5 hours. After the reaction solution was cooled again to −70° C., selenium power (0.47 g, 60 mmol) was gradually added therein over 10 min, and then stirred at the maintained temperature for 30 min. Then, the temperature was increased to −20° C. over 2 hours. At this temperature, methyl iodine (0.5 mL, 8.0 mmol) was added. With dewars on, the temperature of the reaction solution was gradually risen to the room temperature. The reaction completed, thereby precipitating a solid, which was then filtered out (recovery, 0.6 g, 60% of the raw materials). The filtrate solution was extracted with chloroform (20 mL×3), thereby obtaining an extract solution. The extract solution was washed with water (30 mL×3), dried with anhydrous magnesium sulfate, and then concentrated under reduced pressure. The concentrated was fractioned via column chromatography (silica gel, carbon disulfide), whereby a yellow solid was obtained from a fraction of Rf of 0.3. The yellow solid was recrystallized using chloroform thereby obtaining a yellowish needle-like crystal of the targeted bis(3-selenomethyl-4-biphenyl-il)acetylene (compound 2) (0.28 g, 18%).

Melting Point: 165 to 167° C.

Yield: 18% (Raw Material Recovery: 60% (Conversion Rate: 45%)

$^1$H NMR (CDCl$_3$) δ7.62 (d, J=8.0, 2H), 7.61 to 7.57 (m, 4H), 7.52 (d, J=1.2 Hz, 2H), 7.47 (t, J=7.2 Hz, 4H), 7.40 (dd, J=1.2, 8.0 Hz, 2H), 7.39 (t, J=7.2 Hz, 2H).

$^{13}$C NMR 6141.86, 140.32, 136.66, 132.92, 128.89, 127.82, 127.13, 126.28, 124.24, 122.54, 93.84, 6.49.

MS (EI) m/z=518 (M$^+$ based on $^{80}$Se)

$C_{28}H_{22}Se_2(CHCl_3)_{0.5}$ Calculated Value: C, 59.42; H, 3.94. Measured Value: C, 59.21; H, 3.70

Example 3

Synthesis of 2,7-diphenyl-[1]benzoseleno[3,2-b][1]benzoselenophene (compound 3)

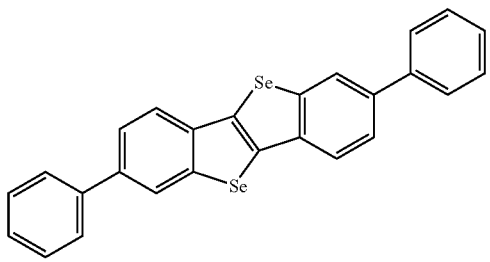

After bis(3-selenomethyl-4-biphenyl-il)acetylene (compound 2) (0.9 g, 1.7 mmol) thus obtained in Example 2 was dissolved in chloroform (20 mL) at the room temperature, iodine (6.9 g, 27 mmol) was added and refluxed for 12 hours. After the reaction was completed, a precipitated solid was filtered out. The resultant solid was washed with saturated sodium hydrogen sulfite aqueous solution so as to remove free iodine, and subsequently washed with water (20 mL), methanol (20 mL), and then hot hexane (20 mL), thereby obtaining 2,7-diphenyl-[1]benzoseleno[3,2-b][1]benzoselenophene (compound 3) (0.75 g, 90%) in a form of white solid. Then, 2,7-diphenyl-[1]benzoseleno[3,2-b][1]benzoselenophene (compound 3) was refined by temperature gradient sublimation under reduced pressure, so as to obtain a material of a device.

Melting Point: >300° C.

$^1$H NMR (CDCl$_3$) δ8.14 (d, J=1.5 Hz, 2H), 7.83 (d, J=8.3 Hz, 2H), 7.65 to 7.68 (m, 6H), 7.46 (t, J=7.6 Hz, 4H), 7.36 (t, J=7.6 Hz, 2H).

MS (EI, 70 eV) m/z=488 (M$^+$ based on $^{80}$Se).

C$_{26}$H$_{16}$Se$_2$ Calculated Value: C, 64.21; H, 3.32%. Measured Value: C, 64.60; H, 3.32%

Example 4

Synthesis of 3-bromo-4-aminobiphenyl (compound 4)

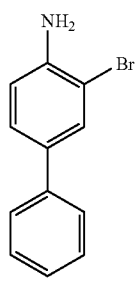

According to a method described in Bumagin, N. A. and Luzikova, E. V. J. Organometallic Chem. 532, 271-273 (1997), 4-aminobiphenyl (18.0 g, 0.1 mol) was synthesized from 4-iode aniline and magnesium phenyl bromide and dissolved in methylene chloride (150 mL). The solution thus obtained was cooled down to 0° C. Into the solution, N-bromosuccinimide (19 g, 0.1 mol) was gradually added and stirred at the room temperature for 12 hours. After the reaction was completed, water (100 mL) was added therein to terminate the reaction. The resultant was extracted with chloroform (50 mL×3) and then washed with water (50 mL×5). The resultant was then dried with anhydrous magnesium sulfate and then distilled under reduced pressure to remove the solvent. The resultant was purified via column chromatography (silica gel, chloroform/hexane (1:1 (v/v), Rf=0.2), thereby obtaining 3-bromo-4-aminobiphenyl (compound 4) in a form of an orange-tan solid. Then, 3-bromo-4-aminobiphenyl (compound 4) was recrystallized using hexane, thereby obtaining an orange-tan needle-like crystal (17.7 g, 72%).

Meting Point: 65 to 67° C.

$^1$H NMR (60 MHz, CHCl$_3$) δ7.61 to 7.15 (m, 7H), 6.68 (d, J=8.2 Hz, 1H), 4.01 (s, 2H)

$^{13}$C NMR (100 MHz, CDCl$_3$) δ143.30, 139.79, 132.74, 130.98, 128.74, 127.02, 126.73, 126.37, 115.87, 109.660;

MS (70 eV, EI) m/z=247 (M$^+$ based on $^{79}$Br)

Example 5

Synthesis of 3-bromo-4-iodobiphenyl (compound 5)

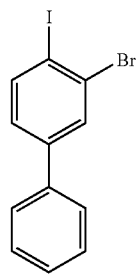

After converting 3-bromo-4-aminobiphenyl (compound 4) (18 g, 70 mmol) to a hydrochloride salt by thermally mixing a concentrated hydrochloric acid (100 mL) thereto, the resultant was cooled down in an ice bath. After dropping saturated sodium nitrite aqueous solution (4.8 g, 70 mmol) therein and stirring the resultant in an ice bath, saturated potassium iodine aqueous solution (2.7 g, 16 mmol) was added therein. Then, the resultant was stirred at 100° C. for 1 hour. The resultant reaction mixture was extracted with chloroform (30 mL×3). The resultant extract solution was then washed with water (30 mL×5) and dried with anhydrous magnesium sulfate. The resultant was fractioned by column chromatography refinement (silica gel, hexane), whereby a yellow oil of 3-bromo-4-iodobiphenyl (compound 5) was obtained (11.5 g, 47%) from the fraction of Rf=0.5.

$^1$H NMR (400 Mz, CDCl$_3$) δ7.86 (d, J=8.3 Hz, 1H), 7.81 (d, J=2.2 Hz, 1H), 7.45 (dt, J=1.5, 7.3 Hz, 2H), 7.41 (dt, J=1.5, 7.3 Hz, 2H), 7.35 (dt, J=1.5, 7.3 Hz, 1H), 7.16 (dd, J=2.2 Hz, J=8.3 Hz, 1H)

$^{13}$C NMR (100 MHz, CDCl$_3$) δ143.30, 139.79, 132.74, 130.98, 128.74, 127.02, 126.73, 126.37, 115.87, 109.66.

MS (70 eV, DI) m/z=358 (M$^+$ based on $^{79}$Br)

C$_{12}$H$_8$BrI Calculated Value: C, 40.15; H, 2.25%. Measured Value: C, 40.00; H, 2.27%

Example 6

Synthesis of bis(3-bromo-4-biphenyl)acetylene (compound 6)

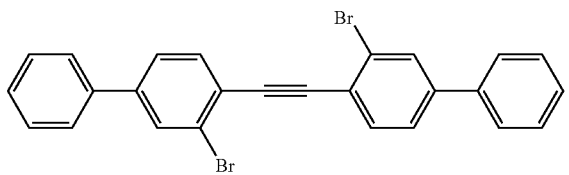

3-bromo-4-iodobiphenyl (compound 5) obtained in Example 5 was dissolved in a mixture solvent of diisopropylamine (20 mL)-benzoic anhydride (20 mL) under nitrogen atmosphere and then deaerated. In the solution thus prepared, trimethylsilylacetylene, (1.1 mL, 7.55 mmol), chloro bis (triphenylphosphine) palladium (0.65 g, 0.93 mmol), cuprous iodide (0.29 g, 1.5 mmol), diazabicycloundecene (DBU, 13.6, 0.90 mmol) and water (0.1 mL, 8.0 mmol) were added and stirred at 60° C. for 18 hours. After the reaction was completed and water (50 mL) was added therein, the resultant was washed with chloroform (50 mL×3) and dried with $MgSO_4$. Using a chloroform-hexane mixture solvent (1:1 (v/v)), the resultant was fractioned so as to concentrate a fraction of Rf=0.5. The concentrated was recrystallized out of chloroform, thereby obtaining targeted bis(3-bromo-4-biphenyl)acetylene (compound 6) in a form of color-less needle-like crystal (1.94 g, 53%).

Melting Point: 187 to 189° C.

$^1$H NMR (400 MHz, $CDCl_3$) δ7.88 (d, J=2.0 Hz, 2H), 7.68 (d, J=6.8 Hz, 1H), 7.59 (m, 4H), 7.54 (dd, J=2.0, 6.8 Hz, 2H), 7.46 (m, 4H), 7.39 (dt, J=1.2, 7.2 Hz, 2H).

MS (EI, 70 eV) m/z=486 ($M^+$ based on $^{79}Br$)

$C_{26}H_{16}Br_2$ Calculated Value: C, 63.96; H, 3.30%. Measured Value: C, 63.17; H, 3.32%.

Example 7

Synthesis of bis(3-selenomethyl-4-biphenylil)acetylene (compound 2)

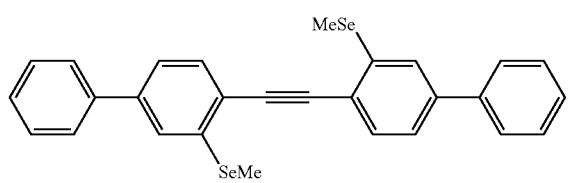

Bis(3-bromo-4-biphenyl)acetylene (compound 6) (0.8 g, 1.6 mmol) obtained from Example 6 was dissolved in anhydrous THF (20 mL) under nitrogen atmosphere and then cooled down to −78° C. In the resultant, t-butyl lithium pentane solution (4.3 mL, 6.6 mmol) was dropped gradually over a period of 10 min or longer. After the resultant was stirred at −78° C. for 30 min, the temperature of the resultant was increased to the room temperature with dewars off. After serene powder (0.26 g, 3.3 mmol) was added therein, the temperature of the resultant was increased to −30° C. After serene was dissolved, methyl iodine (0.2 mL, 3.3 mmol) was added. Then, the temperature of the resultant was gradually returned to the room temperature. After the reaction was completed, the reaction mixture was extracted with chloroform (20 mL×3) and washed with water (20 mL×3). The resultant was dried with anhydrous magnesium sulfate, and then distilled under reduced pressure to remove the solvent. The thus obtained crude product underwent column chromatography refinement (silica gel, carbon disufide, Rf=0.5), thereby obtaining the targeted bis(3-selenomethyl-4-biphenylil)acetylene (compound 2) in a form of yellowish solid. The thus obtained bis(3-selenomethyl-4-biphenylil)acetylene (compound 2) was recrystallized from chloroform, thereby obtaining yellow needle-like crystal (0.7 g, 84%).

Melting Point: 165 to 167° C.

Yield: 18% (Raw Material Recovery 60% (Conversion Rate 45%))

$^1$H NMR ($CDCl_3$) δ7.62 (d, J=8.0, 2H), 7.61 to 7.57 (m, 4H), 7.52 (d, J=1.2 Hz, 2H), 7.47 (t, J=7.2 Hz, 4H), 7.40 (dd, J=1.2, 8.0 Hz, 2H), 7.39 (t, J=7.2 Hz, 2H).

$^{13}$C NMR δ141.86, 140.32, 136.66, 132.92, 128.89, 127.82, 127.13, 126.28, 124.24, 122.54, 93.84, 6.49.

MS (EI) m/z=518 ($M^+$ based on $^{80}Se$).

$C_{28}H_{22}Se_2(CHCl_3)_{0.5}$ Calculated Value: C, 59.42; H, 3.94. Measured Value: C, 59.21; H, 3.70

Example 8

Thin Film Device

Thin film devices illustrated in FIGS. 1(a) and 1(b) were produced, in which the compounds synthesized in Examples described above were used as an organic semiconductor material 4.

More specifically, a contact metal 2 for a gate electrode was formed on a reverse surface of a silicone substrate 1. On the silicone substrate 1, a dielectric layer 3 made of silicon dioxide was formed by thermal oxidation. Contact channels for source 5 and drain 6 were formed on the dielectric layer 3 by electron lithography or photolithography (FIG. 1(a)). On the dielectric layer 3 of the silicone substrate, an organic semiconductor material 4 was further deposited by vacuum deposition with a pressure of approximately $1 \times 10^{-3}$ Pa or less. The vacuum deposition rate was 0.1 nm/s. Substrate temperature was controlled by heating a copper block on which the substrate was placed. The channels had width of 200 μm and a length in a range of 1 to 10 μm. The contact metal of the devices was gold.

In the thin film device having another structure illustrated in FIG. 1(b), a source 5 and a drain 6 were formed on the top surface of the semiconductor layer 4 by using a shadow mask as described above. The source 5 and drain 6 had a width of 1.5 mm and a gap of 0.05 mm.

The thin film devices formed as described above underwent n-doping thereby giving the silicon substrate 1 the function of the gate electrode. Electron field-effect mobility of the devices having the semiconductor layer made of the compound synthesized respectively in the above Examples was measured while applying swept source-drain voltage (0V to −100V) on the devices with a constant a fixed gate voltage. The Electron field-effect mobility was calculated out from saturated drain-source currents on FET response curves.

Figure 2:
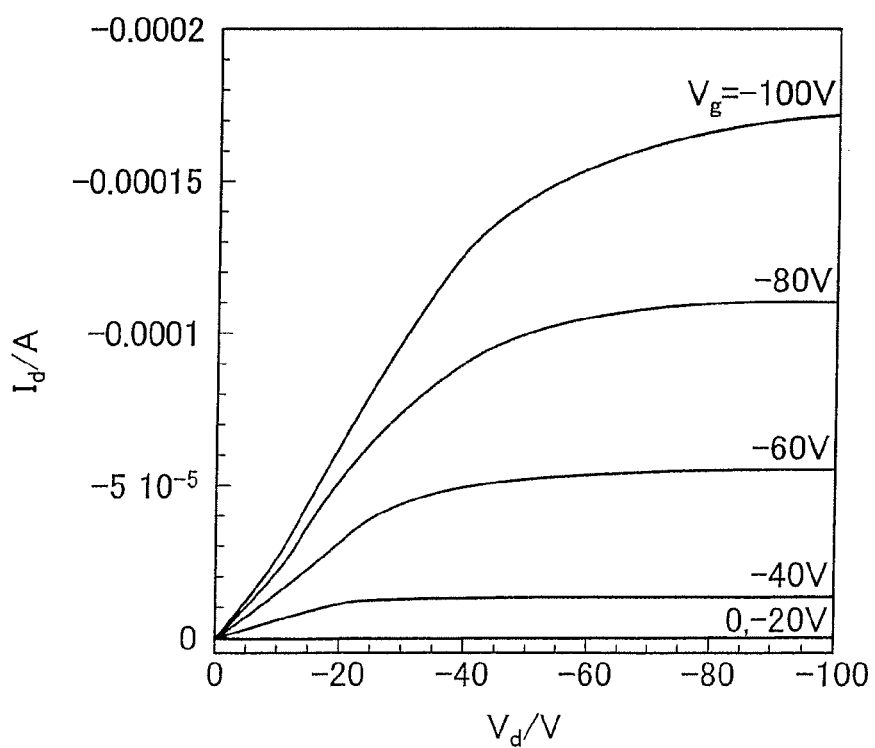
FIG. 2 is a graph plotting an FET response curve of a thin film transistor in which 2,7-diphenylbenzoseleno[2,3-b][1]benzoselenophene was used.

FIG. 2 illustrates the FET response curves obtained from an FET element in which the thin film made of the compound 3 was used. The calculation of the carrier mobility of the semiconductor was carried out according to the description of "Semiconductor Device: Physical Characteristics and Technology" [Sze, S. M., pp 30-35, pp 200-207 (1985)].

Table 1 illustrates results of the measurement of the carrier mobility and ON/OFF current ratio of the semiconductor thin film made of the compound 3. The measurement was carried out using the thin film device having the structure illustrated in FIG. 1(b) and at the room temperature. Table 1 shows average mobility of the attached films at each temperature. Moreover, the ON/OFF current ratio was calculated out from the currents that flew at a ON gate voltage of −100V and at a OFF gate voltage of 0V.

Because mobility of thin films is dependent on the substrate temperature at film formation, that is, the substrate temperature when the film is formed, each thin film device was produced by attaching the organic semiconductor film to the substrate adjusted to the room temperature, 60° C., and 100° C. At each attachment temperature, about ten devices were produced.

TABLE 1

|  | Room Temp. | 60° C. | 100° C. |
|---|---|---|---|
| Mobility (V/cm$^2$S) | 0.20 | 0.31 | 0.17 |
| On/Off Ratio | 10$^6$ | 10$^6$ | 5 × 10$^5$ |
| Threshold Voltage (V) | −18 | −20 | −19 |

As illustrated in Table 1, the semiconductor devices produced with the compound 3 had good threshold voltages, which did not cause an increase in the OFF value. Further, the semiconductor devices had good ON/OFF ratios.

Example 9

2,7-dibromo[1]benzoselenopheno[3,2-b][1]benzoselenophene (compound 7)

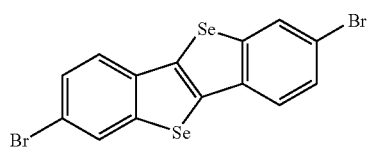

7

The compound 9 (672 mg, 2.0 mmol) was dissolved in chloroform (25 mL) and cooled to 0° C. Into the thus prepared solution, 0.24M bromine solution (chloroform solvent, 25 mL, 3.6 mmol) was dropped, thereby obtaining a reaction mixture, which was then stirred at 2° C. for 10 hours. After that, sodium bisulfite was added in the reaction mixture, thereby precipitating a solid, which was then filtered out and dried. A crude product thus prepared was recrystallized using chlorobenzene, thereby obtaining the compound 7 in the form of colorless crystal (370 mg, 38%), which contained no other isomer.

Melting Point: 278 to 279° C.

$^1$H NMR (400 MHz, CHCl$_3$) δ8.09 (d, J=1.7 Hz, 2H), 7.64 (d, J=8.6 Hz, 2H), 7.56 (dd, J=8.5, 1.5 Hz, 2H);

MS (70 eV, EI) m/z=492 (M$^+$ based on $^{79}$Br, two isotopic patterns were observed for each Se and Br)

C$_{16}$H$_6$Br$_2$Se$_2$ Calculated Value: C, 34.18; H, 1.23, Measured Value: C, 34.00; H, 1.11.

Example 10

Synthesis of 2,7-diphenyl [1]benzoselenopheno[3,2-b][1]benzoselenophene (compound 3)

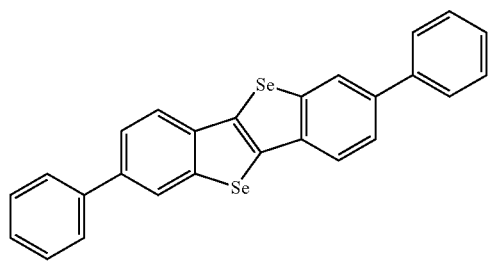

In the present Example, the compound 3 was synthesized via the pathway in which the compound 9 was brominated selectively at 2, and 7 positions, and Suzuki cross-coupling, as described below in detail.

Under nitrogen atmosphere, an aqueous solution (1 mL) of the compound 7 (148 mg, 0.3 mmol) obtained in Example 9, phenylbromic acid (95 mg, 0.8 mmol), and 1 ml of sodium carbohydrate (83 mg, 0.8 mmol) solution was added in THF-toluene mixture solvent (6 mL, 1:1 v/v) and deaerated for 1 hour. After Pd (PPh$_3$)$_4$ (10.5 mg, 3 mol %) was added therein, the solution was thermally refluxed for 12 hours. The reaction mixture thus obtained was mixed with water (10 mL) thereby precipitating a solid, which was then collected by filtration. After being dried, the solid underwent temperature gradient sublimation under reduced pressure, thereby obtaining the targeted compound 3 (56 mg, 38%) in a form of whity-yellow solid.

In the same manner as in Example 8, thin film devices were produced with the compound 3 obtained in the present Example. These thin film devices showed similar performances to the thin film devices of Example 8.

Example 11

2,7-bis(4-trifluorophenyl) [1]benzoseleno[3,2-b](1)benzoselenophene (compound 22)

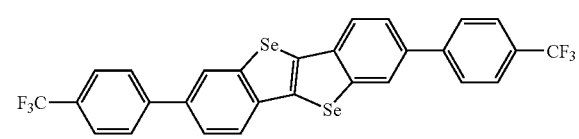

22

The compound 7 (148 mg, 0.3 mmol) obtained in Example 9, 4-trifluoromethylphenylbronic acid (203 mg, 0.8 mmol), sodium carbohydrate (83 mg, 0.8 mmol) dissolved in water (1 mL) were mixed with THF (3 mL) and toluene (3 mL) and deaerated for 1 hour. After that, Pd (PPh$_3$)$_4$ (10.5 mg, 3 mol %) was added therein under nitrogen atmosphere. The resultant was refluxed for 12 hours. After the reflux was completed, water (10 mL) was added therein, thereby precipitating a solid, which was then collected by filtration. The solid was purified by sublimation, thereby obtaining the target compound 22 (87 mg, 47%) in a form of yellow solid.

$^1$H NMR (400 MHz, CS$_2$—CDCl$_3$) δ8.15 (d, J=1.7 Hz, 2H), 7.85 (d, J=8.3 Hz, 2H), 7.76 (d, J=8.5 Hz, 4H), 7.70 (d, J=8.5 Hz, 4H), 7.67 (dd, J=8.3, 1.7 Hz, 2H);

MS (70 eV, EI) M/z=622 (M$^+$ based on $^{80}$Se, two isotopic patterns were observed for Se)

C$_{28}$H$_{14}$F$_6$Se$_2$ Calculated Value: C, 54.04; H, 2.27, Measured Value: C, 53.86; H, 2.16

In the same manner as in Example 8, thin film devices were produced with the compound 22 obtained in the present

Example. These thin film devices showed similar performances to the thin film devices of Example 8.

Example 12 transs-2,2'-bis methylseleno]stilbene (compound 10)

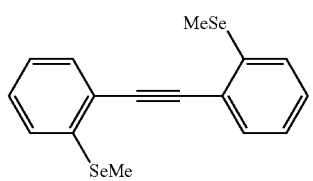

10

According to the method described in the above-mentioned literature (M. Iwaoka et al., J. Am. Chem. Soc. 2004, 126, 5309-5317), 2-methylselenobenzaldehyde (compound 15) was synthesized. A THF solution containing 2-methylselenobenzaldehyde (compound 15) (1.28 g, 6.4 mmol) and THF (10 mL) was prepared. The THF solution was gradually added in a mixture of titanium tetrachloride (1.2 mL) and THF (40 mL) in an ice bath, thereby prepare a reaction mixture. Into the reaction mixture in an ice bath, zinc power (1.28 g) was added at once. Then, the reaction mixture was taken out of the ice bath and its temperature was increased to the room temperature. After that, the reaction mixture was refluxed for 9 hours. After the reaction was completed, the mixture was added to an ice (50 g). Then, saturated sodium hydrogen carbonate aqueous solution (50 mL) and methylene chloride (100 mL) was added therein. The mixture was then stirred for one night. After a resultant precipitated solid was filtered out, a water layer was separated from an organic layer. The water layer was separated by extraction using methylene chloride (20 mL×3). Then, the water layer and the organic layer were mixed together, washed with water (50 mL×2), and then dried with anhydrous magnesium sulfate. Subsequently, the solvent was distilled off, thereby obtaining a crude product. The crude product was purified by column chromatography (silica gel, solvent: methylene chloride, Rf=0.8), thereby obtaining the target compound (compound 10) in a form of while solid (970 mg, 82%).

Melting Point: 84 to 85° C.

$^1$H NMR (400 MHz, CDCl$_3$) δ 7.64 (dd, J=1.4, 7.6 Hz, 2H), 7.47 (dd, J=1.4, 7.6 Hz, 2H), 7.43 (S, 2H), 7.26 (td, J=7.6, 1.4 Hz, 2H), 7.20 (td, J=7.6, 1.4 Hz, 2H)

MS (70 eV, EI) m/z=368 (M$^+$ based on $^{80}$Se, two isotopic patterns were observed for Se)

C$_{16}$H$_{16}$Se$_2$ Calculated Value: C, 52.47; H, 4.40, Measured Value: C, 52.40; H, 4.21.

Example 13

[1]benzoselenopheno[3,2-b][1]benzoselenophene (compound 9)

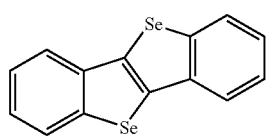

9

The compound 10 (732 mg, 2 mmol) obtained in Example 12 and iodine (2.54 g, 10 mmol) were dissolved in carbon tetrachloride (20 mL). The mixture thus obtained was refluxed for 2 hours. After being cooled, methylene chloride (100 mL) was added in the refluxed. Then, unreacted iodine was filtered away. The resultant filtrate was washed with saturated sodium hydrogen carbonate aqueous solution (50 mL) and water (50 mL) and then dried with anhydrous magnesium sulfate. By distilling off the solvent therefrom, the targeted compound 9 was obtained in a form of whity-yellow solid. The solid was recrystallized using a chloroform-hexane mixture solvent, thereby obtaining colorless crystal (516 mg, 77%).

Example 14

2, 7-diiode[1]benzothieno[3,2-b][1]benzothiophene (compound 21)

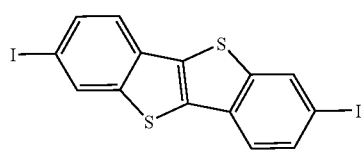

21

According to the above-mentioned literature, S. Y. Zherdeva et al., Zh. Organi. Khimi, 1980, 16, 430-438, a commercially-available compound 17 was converted quantitatively to compound 18 by heating the compound 17 in chlorosulfonic acid. Then, the compound 18 was suspended in acetic acid and heated with 55% hydriodic acid added therein. The resultant precipitated was filtered out once and then added in acetic acid together with bromine. The mixture was heated, thereby obtaining compound 19 as a yellow precipitate. Further, the compound 19 and flaky tin were added in acetic acid and heated. Concentrated hydrochloric acid was gradually added therein, thereby obtaining 2,7-diamino[1]benzothieno[3,2-b][1]benzothiophene (compound 20) as a white precipitate.

The thus synthesized compound 20 (100 mg, 0.37 mmol), water (5 mL), and hydrochloric acid (2.5 mL) were mixed and cooled to 5° C. or below. A solution containing sodium sulfite (52 mg, 0.75 mmol) and water (2 mL), which was separately prepared, was dropped in the mixture while keeping the temperature at 5° C. or below. After the dropping was completed, the mixture was stirred for 30 min. After potassium iodide (125 mg, 0.75 mmol) aqueous solution (2 mL) was then added therein, the mixture was refluxed for 3 hours. After the mixture was cooled down to the room temperature, sodium hydrogen sulfite was added therein, thereby precipitating a solid. The solid was collected by filtration, and then dried, thereby obtaining a crude product (151 mg, 83%) of the compound 21. It was possible to use the crude product in the next reaction (Reaction Formula (11)). Moreover, by recrystallization or sublimation refinement using chlorobenzene as a solvent, a sample for elemental analysis could be obtained.

Melting Point: >300° C.

$^1$H NMR (400 MHz, CDCl$_3$) δ 8.26 (d, J=1.4 Hz, 2H), 7.75 (dd, J=1.4, 8.4 Hz, 2H), 8.16 (d, J=8.4 Hz, 2H)

MS (70 eV, EI) m/z=492 (M$^+$)

$C_{16}H_6I_2S_2$ Calculated Value: C, 34.17; H, 1.23, Measured Value: C, 34.13; H, 1.18.

Example 15

Synthesis of 2,7-diphenyl[1]benzothieno[3,2-b][1]benzothiophene (compound 16)

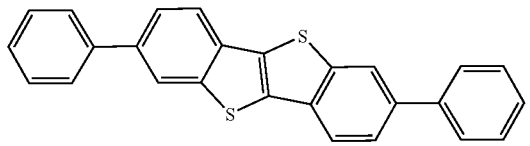

Under nitrogen atmosphere, the compound 21 (246 mg, 0.5 mmol) obtained in Example 14, phenylboronic acid (146 mg, 1.2 mmol), and tripotassium phosphate (170 mg) were added in DMF (10 mL) and deaerated for 30 min. $Pd(PPh_3)_4$ (92.4 mg, 0.08 mmol), and $Ag_2O$ (463 mg, 2.0 mmol) were added therein and stirred at 85° C. for 9 hours. The reaction mixture thus prepared was poured into saturated ammonium chloride aqueous solution (50 mL), consequently precipitating a solid. The solid was filtered out, dried and then continuously extracted with hot chlorobenzene (100 mL). The extract solution was evaporated to dry, and then underwent temperature gradient sublimation under reduced pressure, thereby obtaining the target compound (96 mg, 49%) in a form of a white solid. From this solid, devices in Example 15 were prepared.

Melting Point: >300° C.

$^1$H NMR (400 MHz, $CDCl_3$) δ 8.09 (d, J=1.5 Hz, 2H), 7.91 (d, J=8.1 Hz, 2H), 7.69 (d, J=1.5, 8.1 Hz, 2H), 7.67 (d, J=7.8 Hz, 4H), 7.46 (t, J=7.8 Hz, 4H), 7.35 (t, J=7.8 Hz, 2H).

MS (70 eV, EI) m/z=392 ($M^+$)

$C_{26}H_{16}S_2$ Calculated Value: C, 79.55; H, 4.11, Measured Value: C, 79.25; H, 4.11.

Example 16

Synthesis of 2,7-bis(4-trifluoromethyldiphenyl)[1]benzothieno[3,2-b][1]benzothiophene (compound 23)

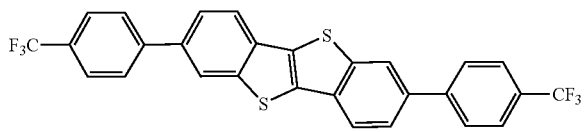

Under nitrogen atmosphere, the compound 21 (246 mg, 0.5 mmol) obtained in Example 14, 4-trifluoromethylphenyl boronic acid (220 mg, 1.15 mmol), and tripotassium phosphate (170 mg) were added in DMF (10 mL) and deaerated for 30 min. After $Pd(PPh_3)_4$ (92.4 mg, 0.08 mmol), $Ag_2O$ (463 mg, 2.0 mmol) were added therein, the mixture thus prepared was stirred at 85° C. for 9 hours. The resultant reaction mixture was poured into a saturated ammonium chloride aqueous solution (50 mL), consequently precipitating a solid. The solid was filtered, dried, and then continuously extracted with hot chlorobenzene (100 mL). The extract solution was evaporated to dry, and underwent temperature gradient sublimation under reduced pressure, thereby obtaining the target compound (compound 23) in a form of a pale yellow solid (134 mg, 50%).

Melting Point: >300° C.

$^1$H NMR (400 MHz, $CDCl_3$) δ 8.15 (d, J=1.5 Hz, 2H), 7.98 (d, J=8.3 Hz, 4H), 7.80 (d, J=8.0 Hz, 4H), 7.73 (d, J=8.0 Hz, 4H), 7.71 (dd, J=8.3, 1.5 Hz, 2H).

MS (70 eV, EI) m/z=528 ($M^+$)

$C_{28}H_{14}F_2S_2$ Calculated Value: C, 63.63; H, 2.67, Measured Value: C, 63.41; H, 2.54.

In the same manner as in Example 8, thin film devices were produced with the compound 23 obtained in the present Example. These thin film devices showed similar performances to the thin film devices of Example 8.

Example 17

Thin Film Device

In the same manner in Example 8, FET devices (thin film devices respectively having the structures illustrated in FIGS. 1(a) and 1(b)) were produced in which the compound obtained in Example 14 was used as the organic semiconductor material 4.

The present Example studied how substrate temperature influenced the device performance. In the present Example, the deposition of the organic material 4 on the silicon substrate 1 was carried out with three substrate temperatures: room temperature, 60° C. and 100° C. Furthermore, FET devices were prepared, some having a substrate in which a surface of an dielectric layer was treated with a toluene solution of octyltrichlorosilane (OTS; a silane coupling agent), and the other having a substrate in which the surface of the dielectric layer was not treated as such.

The FET devices having the structure illustrated in FIG. 1(b) with the thin film made of the compound 16 was measured in the electric field effect mobility in the semiconductor thin film made of the compound 16. The measurement was carried out in the atmosphere and at the room temperature. Table 2 shows the results (averages of three or more devices) of the measurement. The measurement was carried out under the same conditions as in Example 8.

TABLE 2

| | Mobility ($cm^2$/Vs)/On/Off/Ratio | | |
|---|---|---|---|
| | Room Temp. | 60° C. | 100° C. |
| Untreated Substrate | 0.13/$10^6$ | 0.25/$10^7$ | 0.20/$10^7$ |
| OST Treated Substrate | 0.40/$10^7$ | 0.48/$10^8$ | 1.0/>$10^8$ |

As shown in Table 2, the thin film devices produced with the compound 16 were very high in the electric field effect mobility. Moreover, it was found that the OTS treatment increased the electric field effect mobility by 2 to several times. Of all, an electric field effect mobility of 1.0 $cm^2$/Vs was obtained with the OTS treated substrate and the substrate temperature of 100° C. This electric field effect mobility is one of highest values reported for devices using organic semiconductor materials. This also demonstrated that the compound 16 is a very excellent semiconductor material.

Figure 3:
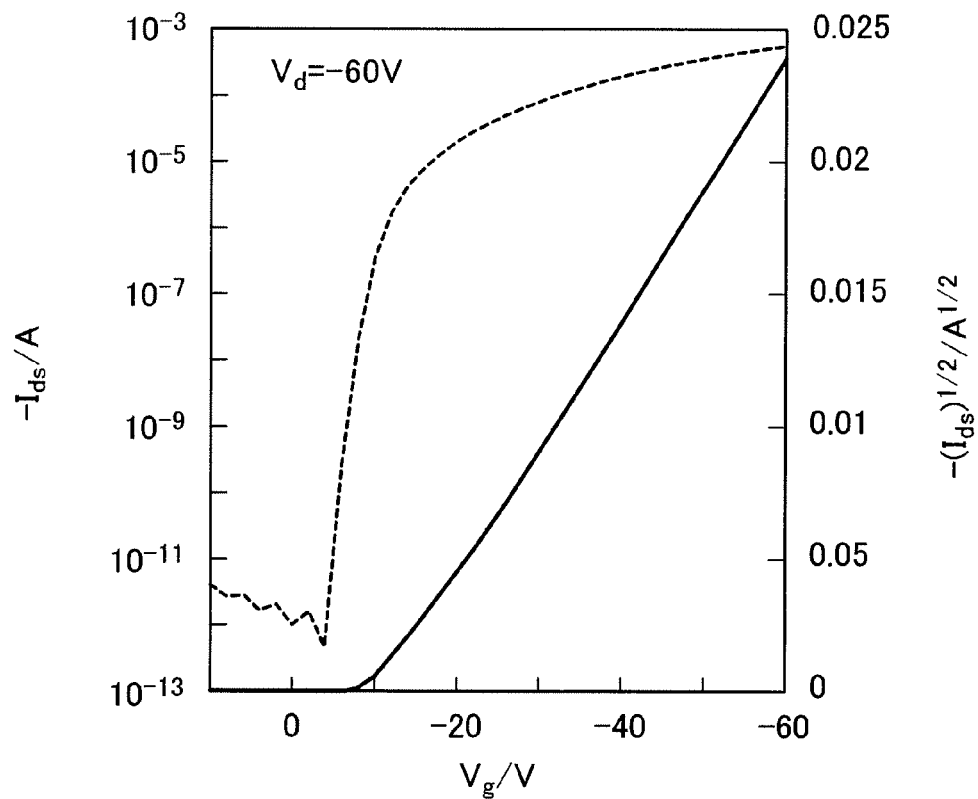
FIG. 3 is a graph plotting a transfer curve of a thin film transistor device (using Si/SiO$_2$ substrate subjected to an OTS treatment; substrate temperature at vapor deposition: 100° C.) in which 2,7-diphenylbenzoseleno[2,3-b][1]benzoselenophene was used.

Moreover, FIG. 3 plots a transfer curve of the FET device having the structure illustrated in FIG. 1(b) with the thin film made of the compound 16. As illustrated in FIG. 3, the device obtained in the present Example was very excellent in the switching property: its current value at off time was (sub-threshold current) as small as 10-12 ampere or less and its ON/OFF ratio (ratio of the current values at the ON and OFF times) was so large that it reached the vicinity of $10^9$. This explained that use of the device obtained in the present Example would provide excellent switching property in a logic circuit or memory circuit in which the device was used. Further, a raise of the current value (sub-threshold swing) from OFF to ON was as steep as approximately 1.0V/dec. This is one of most lowest values reported for devices in which the dielectric layer was a 200 nm $SiO_2$ layer. A semiconductor material having a small sub-threshold swing is essential in producing a VLSI circuit or the like with high quality. Therefore, the material of the present invention is excellent in terms of the sub-threshold properties.

[Stability of Devices in Example 8]

Figure 4:
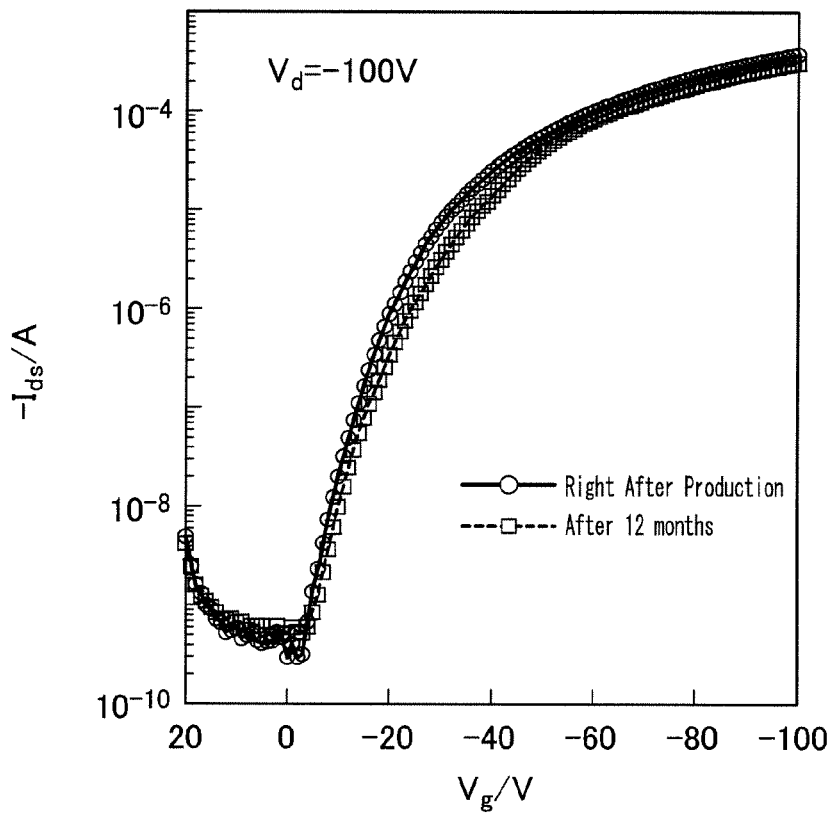
FIG. 4 a graph plotting transfer curves of a thin film transistor in which 2,7-diphenylbenzoseleno[2,3-b][1]benzoselenophene was used. One of the curves is a transfer curve obtained right after production of the device, while the other is a transfer curve obtained 1 year after the production.

The FET devices of Example 8 were subjected to stability test in a long period (12 months). More specifically, transfer curves (FIG. 4) of the FET devices were prepared right after the production thereof and after 12 months therefrom, so as to compare the FET devices right after the production thereof and after 12 months therefrom in terms of FET responding property. As illustrated in FIG. 4, the change in the FET responding property was practically nought between right after the production thereof and after 12 months therefrom. Thus, no deterioration did not occur. That is, the FET device having the thin film made of the compound 3 was very stable.

Figure 5:
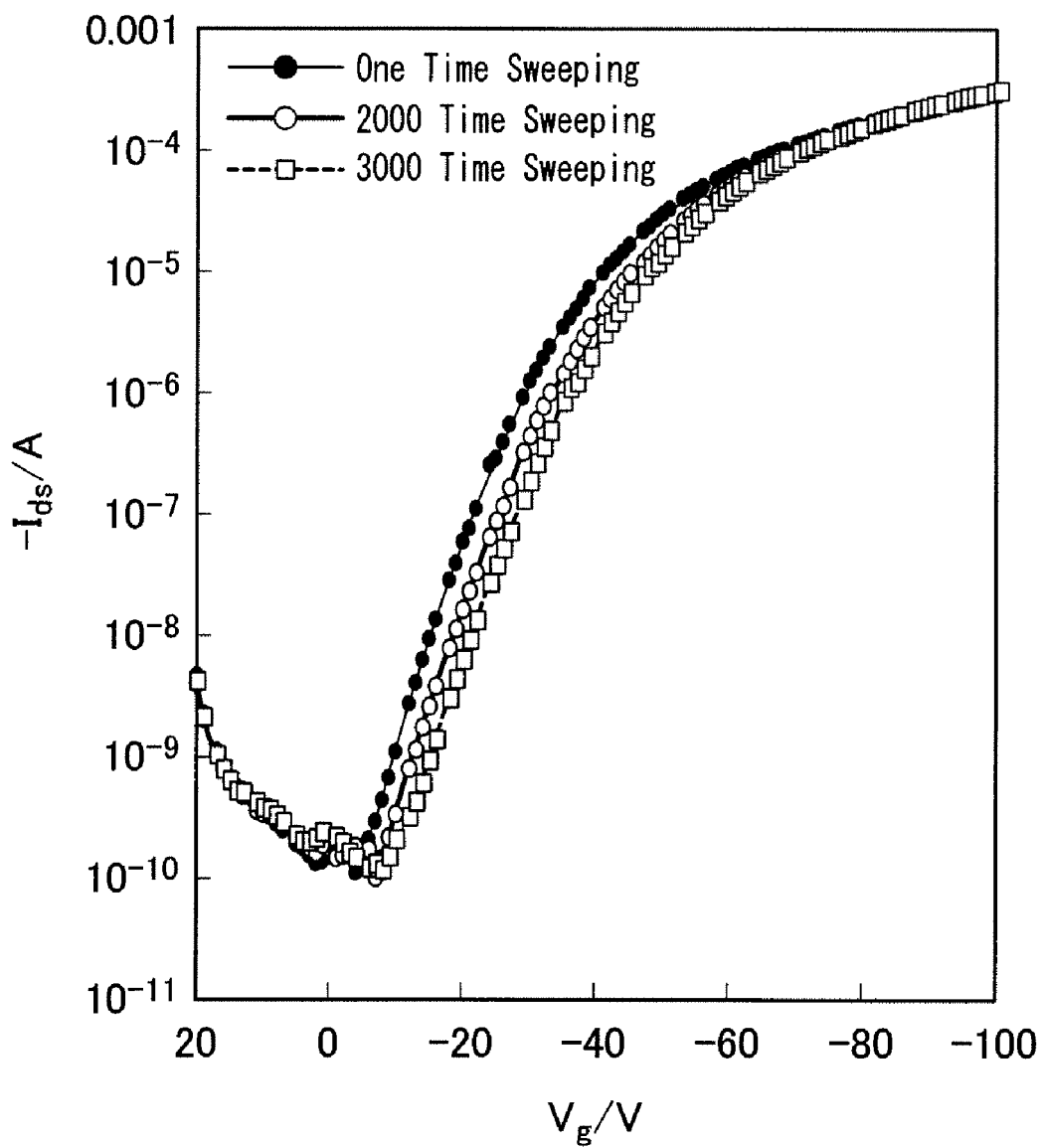
FIG. 5 is a graph plotting transfer curves of a thin film transistor in which 2,7-diphenylbenzoseleno[2,3-b][1]benzoselenophene was used.

Moreover, the FET devices were subjected to durability test in the atmosphere by turning the gate On and Off continuously. More specifically, the source-drain voltage (Vd) was fixed at −100V, and the gate voltage (Vg) was swept from +20V to −100V repeatedly. Transfer curves (FIG. 5) were plotted for the FET devices subjected to the sweeping carried out once, 2000, and 3000 times. As illustrated in FIG. 5, the transfer curve, that is, the FET responding property showed no large change even after 3000-time sweeping. That is, the thin film device provided with the thin film made of the compound 3 was stable against repeated operation.

INDUSTRIAL APPLICABILITY

Impurity contamination in a synthesis process of a novel semiconductor compound according to the present invention is small. Thus, by performing sublimation refinement once, it is possible to a mobility reacting 1.0 $cm^2/Vs$ and a high ON-OFF ratio ($10^6$ or more) in a TFT device in which the novel semiconductor compound was used. Therefore, the present invention makes it possible to easily produce various semiconductor materials having excellent electric, electronic, and photoelectric properties and high solubility.

The invention claimed is:

1. A compound represented by General Formula:

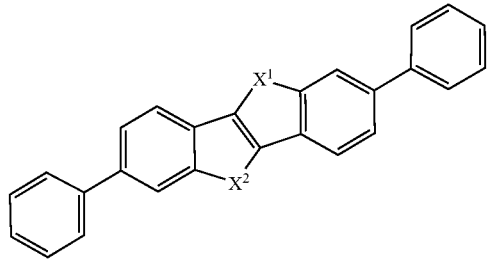

where $X_1$ and $X_2$ are independently Se.

2. A method of producing a compound as set forth in claim 1, the method comprising:

adding iodine in a chloroform solution of a compound represented by:

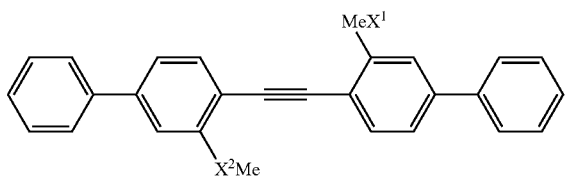

where $X_1$ and $X_2$ are independently Se.

* * * * *